(12) United States Patent
Berry et al.

(10) Patent No.: US 10,933,190 B2
(45) Date of Patent: *Mar. 2, 2021

(54) SYRINGE WITH ROLLING DIAPHRAGM

(71) Applicant: BAYER HEALTHCARE LLC, Whippany, NJ (US)

(72) Inventors: David Berry, Kittanning, PA (US); Kevin Cowan, Allison Park, PA (US); Martin Gibler, West Chester, OH (US); Benjamin Krupp, Cincinnati, OH (US); Vince Delbrugge, Indiana, PA (US); Michael Spohn, Fenelton, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 554 days.

This patent is subject to a terminal disclaimer.

(21) Appl. No.: 15/568,505

(22) PCT Filed: Apr. 22, 2016

(86) PCT No.: PCT/US2016/028824
§ 371 (c)(1),
(2) Date: Oct. 23, 2017

(87) PCT Pub. No.: WO2016/172467
PCT Pub. Date: Oct. 27, 2016

(65) Prior Publication Data
US 2018/0161496 A1 Jun. 14, 2018

Related U.S. Application Data

(60) Provisional application No. 62/257,053, filed on Nov. 18, 2015, provisional application No. 62/152,511, filed on Apr. 24, 2015.

(51) Int. Cl.
*A61M 5/145* (2006.01)
*A61M 5/148* (2006.01)
*A61M 5/00* (2006.01)

(52) U.S. Cl.
CPC ........ *A61M 5/14586* (2013.01); *A61M 5/007* (2013.01); *A61M 5/148* (2013.01);
(Continued)

(58) Field of Classification Search
CPC .............. A61M 5/007; A61M 5/14546; A61M 5/14566; A61M 2005/14553; A61M 5/14586; A61M 5/148; A61M 5/282
See application file for complete search history.

(56) References Cited

U.S. PATENT DOCUMENTS

| 352,715 | A | 11/1886 | Sandmark |
| 798,093 | A | 8/1905 | Edward |

(Continued)

FOREIGN PATENT DOCUMENTS

| EP | 1086661 A2 | 3/2001 |
| EP | 2098258 A1 | 9/2009 |

(Continued)

OTHER PUBLICATIONS

"International Search Report and Written Opinion from PCT/US2016/028824", dated Jul. 27, 2016.
(Continued)

*Primary Examiner* — Theodore J Stigell
(74) *Attorney, Agent, or Firm* — Joseph L. Kent; David Schramm; James R. Stevenson

(57) ABSTRACT

A rolling diaphragm syringe includes a proximal end having an end wall, a distal end having an open-ended discharge neck, a sidewall extending along a longitudinal axis, and a piston engagement portion protruding proximally from a central portion of the end wall and configured for engage-
(Continued)

ment with a piston of a fluid injector. The piston engagement portion has a stem with a first end attached to the end wall, a second end extending proximally from the first end, and at least one protrusion that protrudes radially outward. The sidewall is flexible and rolls upon itself when acted upon by the piston such that an outer surface of the sidewall is folded in a radially inward direction as the piston is advanced from the proximal end to the distal end, and unfolded in a radially outward direction as the piston is retracted from the distal end to the proximal end.

18 Claims, 15 Drawing Sheets

(52) U.S. Cl.
CPC .... *A61M 5/14546* (2013.01); *A61M 5/14566* (2013.01); *A61M 2005/14553* (2013.01)

(56) References Cited

U.S. PATENT DOCUMENTS

| | | |
|---|---|---|
| 937,029 A | 10/1909 | Blessing et al. |
| 2,514,575 A | 7/1950 | Hein et al. |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Lawshe et al. |
| 2,911,972 A | 11/1959 | Elinger |
| 2,935,067 A | 5/1960 | Bouet |
| 2,950,717 A | 8/1960 | Bonet |
| 3,155,281 A | 11/1964 | Stracey |
| 3,161,194 A | 12/1964 | Chapman |
| 3,161,195 A | 12/1964 | Taylor et al. |
| 3,172,577 A | 3/1965 | Hartung |
| 3,190,619 A | 6/1965 | Penney et al. |
| 3,231,139 A | 1/1966 | Bouet |
| 3,301,293 A | 1/1967 | Santelli |
| 3,340,869 A | 9/1967 | Bane |
| 3,390,821 A | 7/1968 | Mullan |
| 3,411,503 A | 11/1968 | Santomieri |
| 3,442,424 A | 5/1969 | Prussin et al. |
| 3,471,058 A | 10/1969 | Latham et al. |
| 3,473,524 A | 10/1969 | Drewe |
| 3,474,844 A | 10/1969 | Lindstrom et al. |
| 3,506,163 A | 4/1970 | Rauh et al. |
| 3,557,788 A | 1/1971 | Swartz |
| 3,613,963 A | 10/1971 | Berkmuller |
| 3,618,846 A | 11/1971 | Poli |
| 3,826,409 A | 7/1974 | Chilcoate |
| 3,873,003 A | 3/1975 | Seiferth et al. |
| 3,938,514 A | 2/1976 | Boucher |
| 4,035,461 A | 7/1977 | Korth |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,171,698 A | 10/1979 | Genese |
| 4,349,129 A | 9/1982 | Amneus |
| 4,392,491 A | 7/1983 | Takasugi et al. |
| 4,411,656 A | 10/1983 | Cornett, III |
| 4,526,296 A | 7/1985 | Berger et al. |
| 4,753,638 A | 6/1988 | Peters |
| 4,773,458 A | 9/1988 | Touzani |
| 4,850,807 A | 7/1989 | Frantz |
| 5,000,739 A | 3/1991 | Kulisz et al. |
| 5,201,438 A | 4/1993 | Norwood |
| 5,209,372 A | 5/1993 | Norwood |
| 5,236,204 A | 8/1993 | Hempel |
| 5,238,150 A | 8/1993 | Williams |
| 5,240,130 A | 8/1993 | Osbakk |
| 5,242,422 A | 9/1993 | Schneberger et al. |
| 5,269,428 A | 12/1993 | Gilbert |
| 5,333,761 A | 8/1994 | Davis et al. |
| 5,353,961 A | 10/1994 | Debush |
| 5,370,250 A | 12/1994 | Gilbert |
| 5,383,858 A | 1/1995 | Reilly et al. |
| 5,397,157 A | 3/1995 | Hempel et al. |
| 5,573,129 A | 11/1996 | Nagata et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,683,369 A | 11/1997 | Tsukada |
| 5,758,789 A | 6/1998 | Shin et al. |
| 5,794,107 A | 8/1998 | Russell |
| 5,827,233 A | 10/1998 | Futagawa et al. |
| 5,836,922 A | 11/1998 | Hansen et al. |
| 5,873,861 A | 2/1999 | Hitchins et al. |
| 5,899,889 A | 5/1999 | Futagawa et al. |
| RE36,377 E | 11/1999 | Gilbert |
| 5,979,326 A | 11/1999 | Ohinata |
| 6,054,194 A | 4/2000 | Kane |
| 6,062,437 A | 5/2000 | Mascitelli |
| 6,077,252 A | 6/2000 | Siegel |
| 6,105,815 A | 8/2000 | Mazda |
| 6,142,976 A | 11/2000 | Kubo |
| 6,216,915 B1 | 4/2001 | Harman et al. |
| 6,224,577 B1 | 5/2001 | Dedola et al. |
| 6,250,505 B1 | 6/2001 | Petit |
| 6,315,761 B1 | 11/2001 | Shcherbina et al. |
| 6,319,235 B1 | 11/2001 | Yoshino |
| 6,322,535 B1 | 11/2001 | Hitchins et al. |
| 6,332,876 B1 | 12/2001 | Poynter et al. |
| 6,485,471 B1 | 11/2002 | Zivitz et al. |
| 6,558,358 B2 | 5/2003 | Rosoff et al. |
| 6,578,738 B1 | 6/2003 | Keller |
| 6,620,134 B1 | 9/2003 | Trombley, III et al. |
| 6,634,524 B1 | 10/2003 | Helmenstein |
| 6,652,489 B2 | 11/2003 | Trocki et al. |
| 6,702,143 B2 | 3/2004 | Wang |
| 6,773,417 B2 | 8/2004 | Fitzgibbons et al. |
| 6,840,164 B2 | 1/2005 | Eastman |
| 6,866,039 B1 | 3/2005 | Wright et al. |
| 6,869,419 B2 | 3/2005 | Dragan et al. |
| RE38,770 E | 8/2005 | Gilbert |
| 7,004,213 B2 | 2/2006 | Hansen |
| 7,011,650 B2 | 3/2006 | Rosoff et al. |
| 7,192,549 B2 | 3/2007 | Hansen |
| 7,250,039 B2 | 7/2007 | Fitzgerald |
| 7,309,463 B2 | 12/2007 | Hansen |
| 7,513,378 B2 | 4/2009 | Mori et al. |
| 7,553,294 B2 | 6/2009 | Lazzaro et al. |
| 7,604,623 B2 | 10/2009 | Brunner et al. |
| 7,666,169 B2 | 2/2010 | Cowan et al. |
| 7,802,691 B2 | 9/2010 | Musalek et al. |
| 9,173,995 B1 | 11/2015 | Tucker et al. |
| 9,180,252 B2 | 11/2015 | Gelblum et al. |
| 9,199,033 B1 | 12/2015 | Cowan et al. |
| 9,474,857 B2 | 10/2016 | Riley et al. |
| 10,105,491 B2 | 12/2018 | Gelblum et al. |
| 10,583,256 B2 * | 3/2020 | Berry ............... A61M 5/14586 |
| 2004/0249344 A1 | 12/2004 | Nemoto et al. |
| 2009/0112087 A1 | 4/2009 | Fago |
| 2010/0091361 A1 | 4/2010 | Yuuki |
| 2012/0020911 A1 | 1/2012 | Seliktar et al. |
| 2012/0209111 A1 | 8/2012 | Cowan et al. |
| 2012/0253291 A1 | 10/2012 | Ivosevic et al. |
| 2013/0023048 A1 | 1/2013 | Kim et al. |
| 2013/0030291 A1 | 1/2013 | Lewis |
| 2013/0211248 A1 | 8/2013 | Cowan et al. |
| 2013/0281940 A1* | 10/2013 | Gelblum ................. B29C 49/10 |
| | | 604/214 |
| 2017/0035974 A1 | 2/2017 | Berry et al. |

(56) References Cited

U.S. PATENT DOCUMENTS

FOREIGN PATENT DOCUMENTS

| | | | |
|---|---|---|---|
| EP | 3057648 | A1 | 8/2016 |
| FR | 1288915 | A | 3/1962 |
| GB | 2214819 | A | 9/1989 |
| GB | 2374143 | A | 10/2002 |
| WO | 9221391 | A1 | 12/1992 |
| WO | 9707841 | A2 | 3/1997 |
| WO | 0204049 | A1 | 1/2002 |
| WO | 2010004206 | A2 | 1/2010 |
| WO | 2010014654 | A1 | 2/2010 |
| WO | 2012061140 | A1 | 5/2012 |
| WO | 2012155035 | A1 | 11/2012 |
| WO | 2014027009 | A1 | 2/2014 |
| WO | 2015058088 | A1 | 4/2015 |
| WO | 2015066506 | A2 | 5/2015 |
| WO | 2015164783 | A1 | 10/2015 |
| WO | 2016058946 | A1 | 4/2016 |
| WO | 2016069711 | A1 | 5/2016 |
| WO | 2016069714 | A1 | 5/2016 |
| WO | 2016172467 | A1 | 10/2016 |

OTHER PUBLICATIONS

"International Preliminary Report on Patentability with Written Opinion from PCT/US2015/027582", dated Nov. 3, 2016.
"International Search Report from PCT/US2015/027582", dated Jul. 28, 2015.
"International Search Report and Written Opinion from PCT Application No. PCT/US2019/016621", dated Apr. 18, 2019.
"Extended European Search Report from EP Application No. 15783517", dated Nov. 8, 2017.
"International Preliminary Report on Patentability, International Search Report and Written Opinion from PCT Application No. PCT/US2016/028824", dated Nov. 2, 2017.

* cited by examiner

SYRINGE WITH ROLLING DIAPHRAGM

CROSS-REFERENCE TO APPLICATIONS

This application is a 371 national phase application of PCT International Application No. PCT/US2016/028824, filed Apr. 22, 2016, and claims priority to U.S. Provisional Patent Application No. 62/152,511, entitled "Syringe With Rolling Diaphragm" and filed on Apr. 24, 2015, and U.S. Provisional Patent Application No. 62/257,053, entitled "Syringe With Rolling Diaphragm" and filed on Nov. 18, 2015, the disclosures of which are incorporated by reference herein in their entirety.

BACKGROUND OF THE DISCLOSURE

Field of the Disclosure

The present disclosure is related to syringes for use in the medical field and, more particularly, to syringes having a flexible sidewall that rolls upon itself when acted upon by a plunger for selectively filling the syringe with a fluid and discharging the fluid from the syringe.

Description of Related Art

In many medical diagnostic and therapeutic procedures, a medical practitioner, such as a physician, injects a patient with one or more medical fluids. In recent years, a number of injector-actuated syringes and powered fluid injectors for pressurized injection of medical fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other imaging procedures. In general, these fluid injectors are designed to deliver a preset amount of fluid at a preset pressure and/or flow rate.

Typically, powered injectors have drive members, such as pistons, that connect to a syringe plunger within the syringe. The syringe generally includes a rigid barrel with the syringe plunger being slidably disposed within the barrel. The drive members drive the plungers in a proximal and/or distal direction relative to a longitudinal axis of the barrel to draw fluid into the syringe barrel or deliver the fluid from the syringe barrel.

It is well known that syringes used in the medical field are typically disposable and are discarded after one use. Although disposable syringes are typically made by mass production methods such as injection molding, such disposable syringes are relatively expensive due to the materials and precision involved in their manufacture and economic costs associated with packaging and shipping. Accordingly, it remains desirable to develop improved designs of syringes to facilitate injection procedures.

SUMMARY OF THE DISCLOSURE

The present disclosure generally relates to syringe assemblies and to methods of forming syringe assemblies. The syringe assemblies may be useful in fluid delivery applications.

In some aspects, a rolling diaphragm syringe may include a proximal end having an end wall for engagement with a piston, a distal end having an open-ended discharge neck, a sidewall extending between the proximal end and the distal end along a longitudinal axis, and a piston engagement portion protruding proximally from a central portion of the outer surface of the end wall and configured for reversible engagement with a piston of a fluid injector. The piston engagement portion may have a stem with a first end attached to the end wall, a second end extending proximally from the first end, and at least one engagement member at or near the second end that protrudes radially outward or radially inward relative to an outer surface of the stem. The sidewall may be flexible and roll upon itself when acted upon by the piston such that an outer surface of the sidewall at a folding region is folded in a radially inward direction as the piston is advanced from the proximal end to the distal end. The outer surface of the sidewall may unroll as the folding region is unfolded in a radially outward direction as the piston is retracted from the distal end to the proximal end.

In other aspects, at least a portion of the end wall may have non-uniform thickness. The thickness of the end wall may continuously increase in thickness in a radially inward direction. The end wall may have a radiused folding edge such that at least a portion of the end wall continuously increases in thickness in a radially inward direction from the radiused folding edge. The discharge neck may have a connection member for connecting to a cap. The at least one engagement member may have a distal surface configured for engaging one or more engagement pins or surfaces of the piston during movement of the piston in the proximal direction. The at least one engagement member may be monolithically formed with the second end of the stem. Alternatively, the at least one engagement member may be attached to the second end of the stem, for example by adhesive, laser welding, or a mechanical or screw type mechanism. Alternatively, the rolling diaphragm syringe may be initially in a compressed, rolled state which is unrolled during a filling process by engaging the rolling diaphragm syringe with a piston and drawing the end wall in a proximal direction.

In other aspects, a syringe for a fluid delivery system may include a pressure jacket having an open distal end, an open proximal end, and a sidewall with a throughbore extending between the distal end and the proximal end. The syringe may further include a rolling diaphragm configured to be received within the throughbore of the pressure jacket. The rolling diaphragm may have a proximal end having an end wall for engagement with a piston, a distal end having an open-ended discharge neck, and a sidewall extending between the proximal end and the distal end along a longitudinal axis. The sidewall of the rolling diaphragm may define an interior volume for receiving a medical fluid therein. The rolling diaphragm further may have a piston engagement portion protruding proximally from a central portion of the end wall and configured for engagement with a piston of a fluid injector. The piston engagement portion may have a stem with a first end attached to the end wall, a second end extending proximally from the first end, and at least one engagement member at or near the second end that protrudes radially outward or radially inward relative to an outer surface of the stem. The syringe may also have a cap configured for engaging at least one of the distal end of the pressure jacket and the distal end of the rolling diaphragm to connect to the open-ended discharge neck of the rolling diaphragm. The sidewall of the rolling diaphragm may be flexible and roll upon itself when acted upon by the piston such that an outer surface of the sidewall at a folding region is folded in a radially inward direction as the piston is advanced from the proximal end to the distal end. The outer surface of the sidewall may unroll as the folding region is unfolded in a radially outward direction as the piston is retracted from the distal end to the proximal end. The at least one engagement member may have a distal surface configured for engaging one or more engagement pins or surfaces of the piston during movement of the piston in the proximal direction. The at least one engagement member may be monolithically formed with the second end of the stem. Alternatively, the at least one engagement member may be attached to the second end of the stem, for example by adhesive, laser welding, or a mechanical or screw type mechanism. An interior of the rolling diaphragm syringe may be pre-filled with the medical fluid. Alternatively, the rolling diaphragm syringe may be initially in a compressed, rolled state which is unrolled during a filling process by engaging the rolling diaphragm syringe with a piston and drawing the end wall in a proximal direction.

In other aspects, the proximal end of the pressure jacket may have at least one locking lip or lug protruding radially outward from an outer surface of the sidewall of the pressure jacket for releasably locking the pressure jacket with a fluid injector. The cap may have at least one projection or groove that interacts with a corresponding groove or projection on the distal end of the pressure jacket for releasably securing the cap to the pressure jacket when the rolling diaphragm syringe is inserted into the distal end of the pressure jacket. The cap may have a nozzle or other fluid discharge port and an annular sidewall surrounding the nozzle or fluid discharge port configured for releasable attachment to a tube set, for example by a luer fit, for delivering the fluid to the interior of the rolling diaphragm syringe during a filling operation and delivering the fluid from the rolling diaphragm syringe to a patient during an injection procedure. The annular sidewall may have one or more gripping elements protruding radially outward from the outer surface of the annular sidewall for gripping an inner surface of the pressure jacket to secure the cap to the pressure jacket. The cap may be non-removably secured to the discharge neck of the rolling diaphragm syringe. The cap may have at least one engagement element for removably connecting the cap with the distal end of the pressure jacket. The cap may be welded to the discharge neck such that the cap is monolithically formed with the discharge neck. Alternatively, the cap may be adhesively bonded to the discharge neck. The protrusion of the piston engagement portion may have a distal surface configured for engaging one or more engagement pins or surfaces of the piston during movement of the piston in the proximal direction. At least a portion of the end wall may have non-uniform thickness. The thickness of the end wall may continuously increase in a radially inward direction. The cap may have a nozzle in fluid communication with the interior volume of the rolling diaphragm syringe, for example through the discharge neck. The nozzle may have a connector for connecting to a fluid path set. The connector may be a luer connector.

In other aspects, a rolling diaphragm syringe for receiving a medical fluid therein may have a proximal end having an end wall for engagement with a piston, a distal end having an open-ended discharge neck, and a sidewall extending between the proximal end and the distal end along a longitudinal axis. The sidewall of the rolling diaphragm syringe may define an interior volume for receiving the medical fluid therein. The rolling diaphragm syringe further may have a piston engagement portion protruding proximally from a central portion of the end wall and configured for engagement with a piston of a fluid injector. The piston engagement portion may have a stem with a first end attached to the end wall, a second end extending proximally from the first end, and at least one engagement member at the second end that protrudes radially outward or radially inward relative to an outer surface of the stem. The rolling diaphragm syringe further may have a cap secured to the discharge neck of the rolling diaphragm syringe. The cap may have a nozzle in fluid communication with the interior volume of the rolling diaphragm syringe. The sidewall of the rolling diaphragm syringe may be flexible and roll upon itself when acted upon by the piston such that an outer surface of the sidewall at a folding region is folded in a radially inward direction as the piston is advanced from the proximal end to the distal end. The outer surface of the sidewall may unroll as the folding region is unfolded in a radially outward direction as the piston is retracted from the proximal end to the distal end.

Various other aspects of the present invention are recited in one or more of the following clauses:

Clause 1: A rolling diaphragm syringe for receiving a medical fluid therein, the rolling diaphragm syringe comprising:
- a proximal end having an end wall for engagement with a piston;
- a distal end having an open-ended discharge neck;
- a sidewall extending between the proximal end and the distal end along a longitudinal axis; and
- a piston engagement portion protruding proximally from a central portion of the end wall and configured for engagement with a piston of a fluid injector, the piston engagement portion having a stem with a first end attached to the end wall, a second end extending proximally from the first end, and at least one engagement member at the second end that protrudes radially outward or radially inward relative to an outer surface of the stem,
- wherein the sidewall is flexible and rolls upon itself when acted upon by the piston such that an outer surface of the sidewall is folded in a radially inward direction as the piston is advanced from the proximal end to the distal end.

Clause 2: The rolling diaphragm syringe of clause 1, wherein at least a portion of the end wall has non-uniform thickness.

Clause 3: The rolling diaphragm syringe of clause 1 or clause 2, wherein the outer surface of the sidewall is unfolded in a radially outward direction as the piston is retracted from the distal end to the proximal end.

Clause 4: The rolling diaphragm syringe of any of clauses 1-3, wherein the end wall has a radiused folding edge and wherein at least a portion of the end wall continuously increases in thickness in a radially inward direction from the radiused folding edge.

Clause 5: The rolling diaphragm syringe of any of clauses 1-4, wherein the discharge neck has a connection member for connecting to a cap.

Clause 6: The rolling diaphragm syringe of any of clauses 1-5, wherein the protrusion has a distal surface configured for engaging one or more engagement pins of the piston during movement of the piston in the proximal direction.

Clause 7: The rolling diaphragm syringe of any of clauses 1-6, wherein the protrusion is monolithically formed with the second end of the stem.

Clause 8: The rolling diaphragm syringe of any of clauses 1-7, wherein the rolling diaphragm is initially in a compressed, rolled state and is configured to be unrolled during a filling process as the piston retracts the end wall in a proximal direction.

Clause 9: A syringe assembly for a fluid delivery system, the syringe assembly comprising:
a pressure jacket having an open distal end, an open proximal end, and a sidewall with a throughbore extending between the distal end and the proximal end;
a rolling diaphragm syringe configured to be received within the throughbore of the pressure jacket, the rolling diaphragm syringe comprising:
a proximal end having an end wall for engagement with a piston;
a distal end having an open-ended discharge neck;
a sidewall extending between the proximal end and the distal end along a longitudinal axis, the sidewall of the rolling diaphragm syringe defining an interior volume for receiving a medical fluid therein; and
a piston engagement portion protruding proximally from a central portion of the end wall and configured for engagement with a piston of a fluid injector, the piston engagement portion having a stem with a first end attached to the end wall, a second end extending proximally from the first end, and at least one engagement member at the second end that protrudes radially outward or radially inward relative to an outer surface of the stem; and
a cap configured for engaging at least one of the distal end of the pressure jacket and the distal end of the rolling diaphragm syringe to enclose the open-ended discharge neck of the rolling diaphragm syringe,
wherein the sidewall of the rolling diaphragm syringe is flexible and rolls upon itself when acted upon by the piston such that an outer surface of the sidewall is folded in a radially inward direction as the piston is advanced from the proximal end to the distal end.

Clause 10: The syringe assembly of clause 9, wherein the proximal end of the pressure jacket has at least one locking lip or lug protruding radially outward from an outer surface of the sidewall of the pressure jacket for releasably locking the pressure jacket with a fluid injector.

Clause 11: The syringe assembly of clause 9 or clause 10, wherein the cap has at least one projection or groove that interacts with a corresponding groove or projection on the distal end of the pressure jacket for releasably securing the cap to the pressure jacket.

Clause 12: The syringe assembly of any of clauses 9-11, wherein the cap has a nozzle and an annular sidewall surrounding the nozzle, the sidewall having one or more gripping elements protruding radially outward from the outer surface of the annular sidewall.

Clause 13: The syringe assembly of any of clauses 9-12, wherein the cap is non-removably secured to the discharge neck of the rolling diaphragm syringe and wherein the cap has an engagement element for removably connecting the cap with the distal end of the pressure jacket.

Clause 14: The syringe assembly of any of clauses 9-13, wherein the outer surface of the sidewall is unfolded in a radially outward direction as the piston is retracted from the distal end to the proximal end.

Clause 15: The syringe assembly of any of clauses 9-14, wherein the protrusion of the piston engagement portion has a distal surface configured for engaging one or more engagement pins of the piston during movement of the piston in the proximal direction.

Clause 16: The syringe assembly of any of clauses 9-15, wherein at least a portion of the end wall has non-uniform thickness.

Clause 17: The syringe assembly of clause 16, wherein the thickness of the end wall continuously increases in a radially inward direction.

Clause 18: The syringe assembly of any of clauses 9-17, wherein the cap has a nozzle in fluid communication with the interior volume of the rolling diaphragm syringe, the nozzle having a connector for connecting to a fluid path set.

Clause 19: The syringe assembly of clause 18, wherein the connector is a luer connector.

Clause 20: A rolling diaphragm syringe for receiving a medical fluid therein, the rolling diaphragm syringe comprising:
a proximal end having an end wall for engagement with a piston;
a distal end having an open-ended discharge neck;
a sidewall extending between the proximal end and the distal end along a longitudinal axis, the sidewall of the rolling diaphragm syringe defining an interior volume for receiving the medical fluid therein;
a piston engagement portion protruding proximally from a central portion of the end wall and configured for engagement with a piston of a fluid injector, the piston engagement portion having a stem with a first end attached to the end wall, a second end extending proximally from the first end, and at least one engagement member at the second end that protrudes radially outward or radially inward relative to an outer surface of the stem; and
a cap secured to the discharge neck of the rolling diaphragm syringe, the cap having a nozzle in fluid communication with the interior volume of the rolling diaphragm syringe,
wherein the sidewall is flexible and rolls upon itself when acted upon by the piston such that an outer surface of the sidewall at a folding region is folded in a radially inward direction as the piston is advanced from the proximal end to the distal end and wherein the outer surface of the sidewall unrolls as the folding region is unfolded in a radially outward direction as the piston is retracted from the distal end to the proximal end.

Further details and advantages of the various aspects described in detail herein will become clear upon reviewing the following detailed description of the various aspects in conjunction with the accompanying drawing figures.

DETAILED DESCRIPTION OF THE INVENTION

Figure 1:
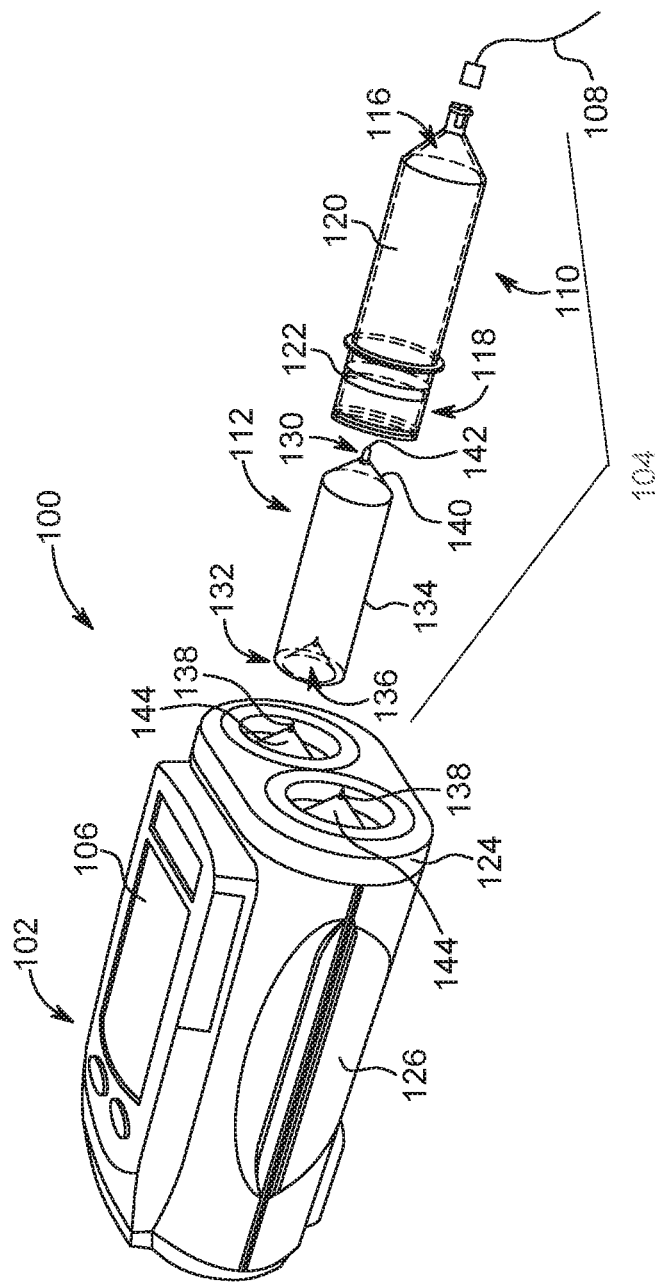
FIG. 1 is a perspective view of a fluid injection system according to one aspect of the present disclosure.

The illustrations generally show preferred and non-limiting aspects of the systems and methods of the present disclosure. While the description presents various aspects of the devices, it should not be interpreted in any way as limiting the disclosure. Furthermore, modifications, concepts, and applications of the disclosure's aspects are to be interpreted by those skilled in the art as being encompassed, but not limited to, the illustrations and descriptions herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe, a pressure jacket, and/or a rolling diaphragm syringe, the term "proximal" refers to a portion of a syringe, a pressure jacket, and/or a rolling diaphragm syringe nearest to an injector when a syringe, a pressure jacket, and/or a rolling diaphragm syringe is oriented for connecting to an injector. The term "distal" refers to a portion of a syringe, a pressure jacket, and/or a rolling diaphragm syringe farthest away from an injector when a syringe, a pressure jacket, and/or a rolling diaphragm syringe is oriented for connecting to an injector. The term "radial" refers to a direction in a cross-sectional plane normal to a longitudinal axis of a syringe, a pressure jacket, and/or a rolling diaphragm syringe extending between proximal and distal ends. The term "circumferential" refers to a direction around an inner or outer surface of a sidewall of a syringe, a pressure jacket, and/or a rolling diaphragm syringe. The term "axial" refers to a direction along a longitudinal axis of a syringe, a pressure jacket, and/or a rolling diaphragm syringe extending between the proximal and distal ends. The term "flexible", when used in connection with a rolling diaphragm syringe, means that at least a portion of a rolling diaphragm syringe, such as a sidewall of a rolling diaphragm syringe, is capable of bending or being bent to change a direction in which it extends. The terms "roll over", "rolling over", and "rolls upon itself" refer to an ability of a first portion of a rolling diaphragm syringe, such as a proximal portion of a sidewall of a rolling diaphragm syringe, to bend approximately 180 relative to a second portion of a rolling diaphragm syringe, such as a distal portion of a sidewall of a rolling diaphragm syringe, when urged by a piston of a fluid injector. It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects (i.e., aspects, variants, variations) disclosed herein are not to be considered as limiting.

Referring to the drawings in which like reference characters refer to like parts throughout the several views thereof, the present disclosure is generally directed to syringe configured as a rolling diaphragm syringe.

With reference to FIG. 1, a fluid delivery system 100 may have a fluid injector 102, such as an automated or powered fluid injector, adapted to interface with and actuate at least one rolling diaphragm syringe 112 and pressure jacket 110, as described herein, each of which may be independently filled with a medical fluid, such as contrast media, saline solution, or any desired medical fluid. The injector 102 may be used during a medical procedure to inject the medical fluid into the body of a patient by driving a plunger 144 into the at least one rolling diaphragm syringe 112 with at least one piston 138. The injector 102 may be a multi-rolling diaphragm syringe injector, wherein two or more rolling diaphragm syringes 112 with corresponding pressure jackets 110 may be oriented in a side-by-side or other relationship and include corresponding plungers 144 separately actuated by respective pistons associated with the injector 102. In aspects with two rolling diaphragm syringe/pressure jackets arranged in a side-by-side relationship and filled with two different medical fluids, the injector 102 may be configured to deliver fluid from one or both of the rolling diaphragm syringes 112.

The injector 102 may be enclosed within a housing 126 formed from a suitable structural material, such as plastic or metal. The housing 126 may be of various shapes and sizes depending on the desired application. For example, the injector 102 may be a free-standing structure configured to be placed on the floor or may be a smaller design for placement on a suitable table or support frame. The injector 102 includes at least one port for interfacing the at least one rolling diaphragm syringe 112 and pressure jacket 110 to respective pistons.

At least one fluid path set 108 may be fluidly connected with a nozzle 130 of the at least one syringe assembly 104 comprising a rolling diaphragm syringe 112 and pressure jacket 110 for delivering medical fluid from the at least one rolling diaphragm syringe 112 through tubing connected to a catheter, needle, or other fluid delivery connection (not shown) inserted into a patient at a vascular access site. Fluid flow into and from the at least one syringe assembly 104 may be regulated by a fluid control module (not shown). The fluid control module may operate various pistons, valves, and/or flow regulating structures to regulate the delivery of the medical fluid, such as saline solution and contrast, to the patient based on user selected injection parameters, such as injection flow rate, duration, total injection volume, and/or ratio of contrast media and saline. One example of a suitable front-loading fluid injector that may be used or modified for use with the herein-described system including at least one rolling diaphragm syringe 112 and at least one interface for loading and releasable retaining of the at least one rolling diaphragm syringe 112 and the pressure jacket 110 with the fluid injector 102 described herein with reference to FIG. 1 is disclosed in U.S. Pat. No. 5,383,858 to Reilly et al. which is incorporated by reference in its entirety. Another example of relevant multi-fluid delivery systems that may be used or modified for use with the present system are found in U.S. Pat. No. 7,553,294 to Lazzaro et al.; U.S. Pat. No. 7,666,169 to Cowan et al.; International Patent Application No. PCT/US2012/037491 (published as WO 2012/155035); U.S. Patent Application Publication No. 2014/0027009 to Riley et al.; and International Patent Application No. PCT/US2015/027582 to Berry et al., all of which are assigned to the assignee of the present application, and the disclosures of which are incorporated herein by reference. Other examples may include new fluid injector systems designed to include various aspects of the rolling diaphragm syringe 112 described herein.

Figure 2:
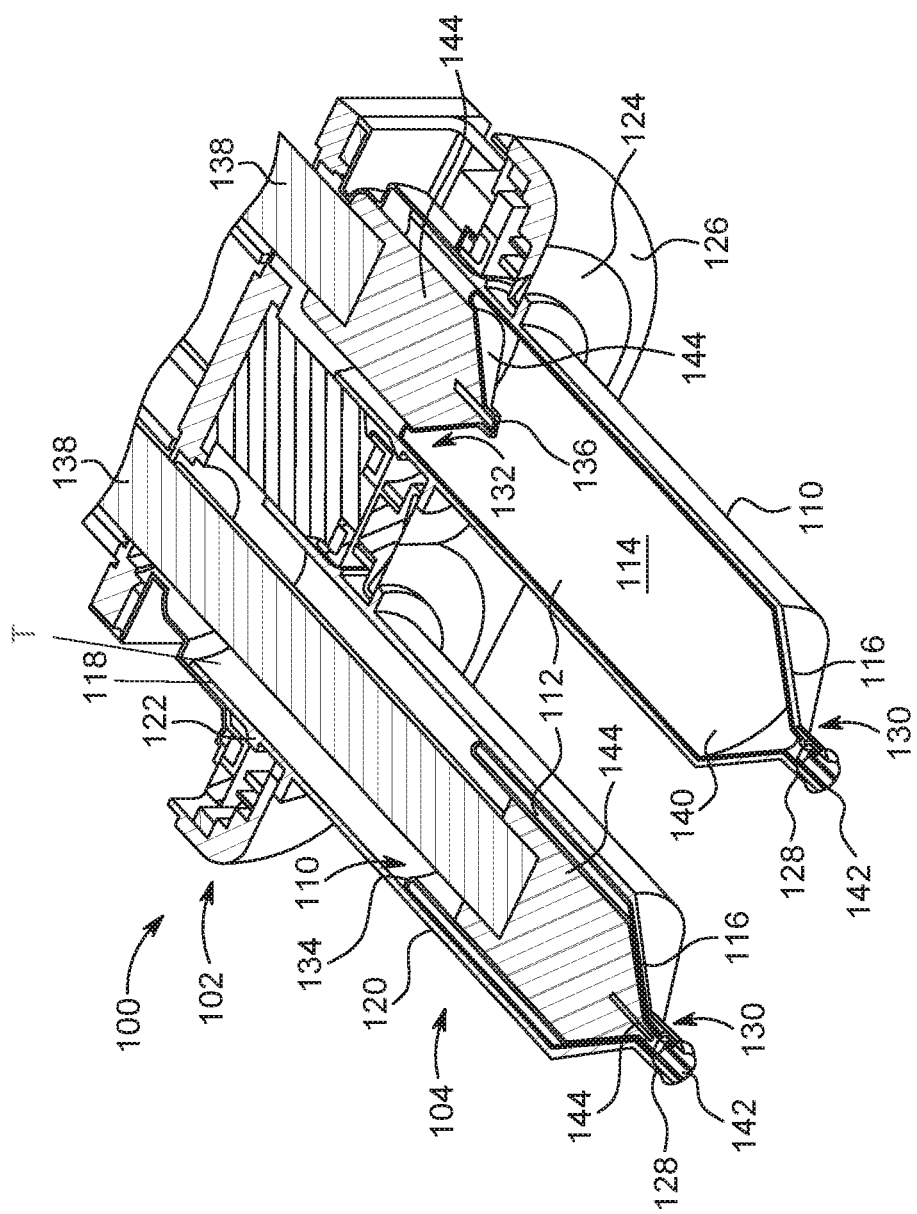
FIG. 2 is a perspective, cross-sectional view of a portion of the fluid injection system shown in FIG. 1 with two rolling diaphragm syringes and pressure jackets connected to a fluid injector.

FIG. 2 is a perspective, cross-sectional view of a portion of the fluid injector 102 shown in FIG. 1. With reference to FIG. 2, the syringe assembly 104 generally includes a cylindrical body or pressure jacket 110 and a rolling diaphragm syringe 112 that interfaces with the pressure jacket 110. As will be described hereinafter, the rolling diaphragm syringe 112 defines an interior volume 114 for receiving a fluid therein and/or dispensing a fluid therefrom. The rolling diaphragm syringe 112 is configured for being inserted into at least a portion of the pressure jacket 110 and the pressure jacket 110 is configured for engagement with fluid injector 102. The syringe assembly 104 is adapted for use in CT, MRI, PET, and like procedures and operable at typical operating pressures of, for example, about 10-400 psi, such as 200-400 psi, depending on the viscosity of the fluid and the desired rate of injection. In some aspects, the rolling diaphragm syringe 112 may be a bladder syringe described in U.S. Patent Application Publication No. 2013/0211248, entitled "Bladder Syringe Fluid Delivery System", or a syringe described in U.S. Pat. No. 9,180,252, entitled "Bellows Syringe Fluid Delivery System", the disclosures of which are incorporated herein by reference in their entirety.

The cylindrical body of pressure jacket 110 may be a unitary, typically cylindrical body having a distal end 116 and a proximal end 118 with a throughbore T extending between the distal end 116 and the proximal end 118. The pressure jacket 110 is typically a reusable component, while the rolling diaphragm syringe 112 is typically a single-use component. In another aspect, the rolling diaphragm syringe 112 may be reusable such that the rolling diaphragm syringe 112 is refillable with fluid. For example, the rolling diaphragm syringe 112 can be pre-filled with fluid, or can be initially empty, and can be filled and/or refilled one or more times. When the rolling diaphragm syringe 112 is initially empty, it may be initially in the compressed state where it may be filled with the fluid by proximal retraction of the proximal end wall; or alternatively, the rolling diaphragm syringe 112 may be in the uncompressed state and may be filled with the fluid, for example through a discharge neck 140 or through a nozzle or outlet port in a distal end cap. In another aspect, both the pressure jacket 110 and the rolling diaphragm syringe 112 may be single-use components that are disposed of after each patient use. In this aspect, both the pressure jacket 110 and the rolling diaphragm syringe 112 are disposed of after use and a new pressure jacket 110 and rolling diaphragm syringe 112 are loaded into the fluid injector 102 for subsequent use. The pressure jacket 110 has a sidewall 120 that defines a throughbore T between the distal and proximal ends 116, 118. An inner surface of the throughbore T may be smooth, textured, or a combination thereof. The proximal end 118 is adapted to interface with the fluid injector 102 and includes one or more mounting structures 122 positioned to engage a locking mechanism at the front end or face plate 124 of the housing 126 of the fluid injector 102 to properly seat the pressure jacket 110 relative to the fluid injector 102. As an example, two opposed bayonet attachment flanges may be provided on the proximal end 118 for interfacing with the fluid injector face plate 124 to secure the pressure jacket 110 to the fluid injector 102. In some aspects, the pressure jacket 110 may have a connection member to releasably secure the pressure jacket to the fluid injector 102 in the form of a connection member described in U.S. Pat. No. 9,173,995, entitled "Self-Orienting Syringe and Syringe Interface", in U.S. Pat. No. 9,199,033, entitled "Self-Orienting Syringe and Syringe Interface", International Application No. PCT/US2015/057751, filed Oct. 28, 2015, or International Application No. PCT/US2015/057747, filed Oct. 28, 2015, the disclosures of which are incorporated herein by reference in their entirety. In another aspect, an adapter may be provided for connecting the pressure jacket 110 and rolling diaphragm syringe 112 to the fluid injector 102.

The distal end 116 of the pressure jacket 110 may include a substantially frusto-conical portion or be configured to connect with a substantially frusto-conical cap portion, each of which may terminate in an outlet port 128. The pressure jacket 110 may be made of any suitable medical grade material, such as but not limited to a medical grade metal, medical grade composite material, or medical grade plastic material, desirably a clear plastic material, such as, but not limited to, polycarbonate, acrylic, or polyester. In some aspects, the pressure jacket 110 may be releasably secured to the fluid injector 102, for example but not limited to, by a retractable pin that extends through an opening of the pressure jacket 110 to prevent rotation of the pressure jacket 110 when it has been loaded onto the fluid injector 102, for example when attaching or detaching a cap portion to the distal end of the pressure jacket. In other aspects, the pressure jacket 110 may have one or more legs that engage the housing of the fluid injector 102 to prevent rotation of the pressure jacket 110 when it had been loaded onto the fluid injector 102. In further aspects, a sliding collar may be provided around an outer circumference of the pressure jacket 110. The sliding collar desirably engages an expandable ring to expand the ring against a corresponding locking feature of the fluid injector 102 to lock the pressure jacket 110 with the fluid injector 102.

Figure 3:
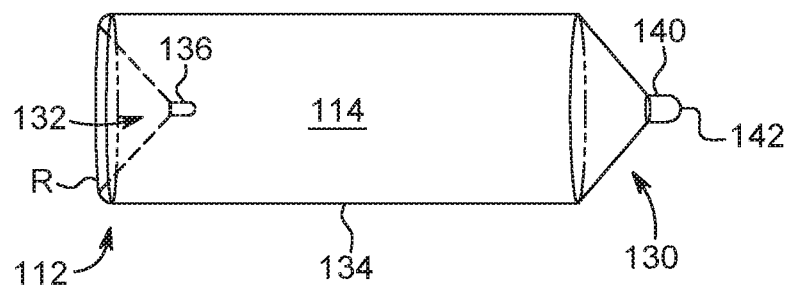
FIG. 3 is a side view of a rolling diaphragm syringe in accordance with one aspect of the present disclosure.

With reference to FIG. 3, and with continuing reference to FIG. 2, the rolling diaphragm syringe 112 generally includes a hollow body that includes a forward or distal end 130, a rearward or proximal end 132, and a flexible sidewall 134 extending therebetween. The proximal end 132 defines a closed end wall 136. The closed end wall 136 may be shaped to interface directly with the piston 138 of the fluid injection, which also acts as a plunger 144. For example, the closed end wall 136 may define a receiving end pocket R for interfacing directly with a similarly-shaped piston 138. In particular aspects, the piston 138 may be shaped to substantially match the shape of the closed end wall 136 or, alternatively, pressure from the piston 138 as it moved distally may conform the end wall 136 to substantially match the shape of the piston 138. The closed end wall 136 may alternatively include an attached rigid base element for engaging with the piston 138 in a like manner, as described herein. In one aspect, the proximal end 132 and/or the distal end 130 of the rolling diaphragm syringe 112 may be more rigid relative to the sidewall 134. The sidewall 134 may have a smooth, substantially uniform structure, or it may have one or more ribs provided thereon to facilitate the rollover during an injection procedure. In some aspects, the sidewall 134 and/or the end wall 136 may have a textured surface, or a combination of a smooth surface and a textured surface. One or more indicia (not shown) may be formed on the sidewall 134. In another aspect, the sidewall 134 may have a non-uniform thickness along its longitudinal length to facilitate the rolling over of the sidewall 134. For example, the sidewall 134 at or near the proximal end 132 may be thinner than the sidewall 134 at or near the distal end 130 to facilitate rolling of the sidewall 134 from the proximal end 132 toward the distal end 130. The thicker sidewall 134 at or near the distal end 130 may function as the pressure jacket 110 and may not roll over. In specific aspects, the sidewall 134 at or near the distal end 130 may be substantially rigid.

The rearward or proximal portion of the sidewall 134 connects to the closed end wall 136, and a forward or distal portion of the sidewall 134 defines a discharge neck 140 opposite the closed end wall 136. The closed end wall 136 may have a non-uniform thickness, for example in a radial direction extending from a central longitudinal axis of the rolling diaphragm syringe 112. In certain aspects, at least a portion of the end wall 136 may be thicker near the center and thinner near the connection with the sidewall 134. In other aspects, the discharge neck 140 is adapted to be received in the interior portion of the distal end 116 of the pressure jacket 110 such that the discharge neck 140 is aligned with the outlet port 128 of the pressure jacket 110 or cap 390. The distal end 130 of the rolling diaphragm syringe 112 may be secured permanently within the interior of the pressure jacket 110, adhesively secured therein, or be removably secured therein such as by a friction fit connection or other suitable mechanical connection, such as by securing at the distal end of the pressure jacket 110. The distal end 130 may have a frusto-conical shape that gradually narrows from the sidewall 134 to the discharge neck 140. In certain aspects, the discharge neck 140 may terminate in a discharge port 142 that may have, according to one non-limiting aspect, a fracturable seal (discussed herein) for sterility purposes, such as piercable foil or an elastomeric seal.

The sidewall 134 of the rolling diaphragm syringe 112 defines a soft, pliable or flexible, yet self-supporting body that is configured to roll upon itself, as a "rolling diaphragm", under the action of the piston 138 and/or plunger 144. In particular, as shown in FIG. 2, the sidewall 134 of the rolling diaphragm syringe 112 is configured to roll such that its outer surface is folded and inverted in a radially inward direction as the piston 138 is moved in a distal direction and unroll and unfold in the opposite manner in a radially outward direction as the piston 138, for example a piston releasably attached to the proximal end of the end wall 136, is retracted in a proximal direction. With reference to FIG. 3, the closed end wall 136 may have a concave shape to facilitate the initiation of the inversion or rolling of the sidewall 134 and/or to provide a receiving pocket to receive a distal end of piston 138.

The rolling diaphragm syringe 112 may be made of any suitable medical-grade plastic or polymeric material, desirably a clear or substantially translucent plastic material, such as, but not limited to, polypropylene random copolymer, polypropylene impact copolymer, polypropylene homopolymer, polypropylene, polyethylene terephthalate, POM, ABS, HPDE, nylon, cyclic olefin copolymer, multilayer polypropylene, polycarbonate, ethylene vinyl acetate, polyethylene, and the like. The material of the rolling diaphragm syringe 112 is desirably selected to meet the required tensile and planar stress requirements, water vapor transmission, and chemical/biological compatibility. In some aspects, the rolling diaphragm syringe 112 may have at least one electro-active polymer layer that expands or contracts in response to an application of an electrical voltage. The electro-active polymer layer may be activated to expand or contract the sidewall 134 of the rolling diaphragm syringe 112 to disengage or engage the piston 138. In some aspects, the electro-active polymer layer may be made from a NAFION™ or FLEMION™ materials. In various aspects, the clear plastic material may withstand sterilization procedures, such as exposure to ethylene oxide or electromagnetic radiation sterilization procedures.

The rolling diaphragm syringe 112 according to various aspects herein may be made by a blow-fill-cap (BFC) technique, also referred to in the relevant field of endeavor as a blow-mold-seal (BFS) technique, wherein the rolling diaphragm syringe 112 is blow-molded, optionally filled with the desired medical fluid, such as saline or contrast media, and aseptically sealed by sealing the discharge port 142 with an integrally formed/molded rupture-ready seal, as will be described hereinafter. Alternatively, the rolling diaphragm syringe 112 may be compressed into a compressed state and packaged in a sterilizable packing material for shipping, with optional sealing of the syringe to prevent contamination. The BFC/BFS techniques permit the rolling diaphragm syringe 112 to be formed and optionally filled, and sealed typically in one machine or apparatus. These steps may be accomplished under sterility maintained conditions, limiting the possibility of introducing contaminates in the formed, filled, and sealed rolling diaphragm syringe 112. The entire assembly may be autoclaved or otherwise treated for sterilization, such as by irradiation. The rupture-ready seal is formed as part of the molding process at the conclusion of the filling of the rolling diaphragm syringe 112. A sterility-enhanced preformed and prefilled rolling diaphragm syringe 112 results from the BFC/BFS process. The rupture-ready seal may be designed for external removal or puncture by a user, or may be designed to reliably burst when a preset internal pressure is reached in the rolling diaphragm syringe 112 as the piston 138 moves distally or forward in the rolling diaphragm syringe 112. In another aspect, the rolling diaphragm syringe 112 may be ruptured by a piercing element provided on the pressure jacket 110. In another aspect, the rolling diaphragm syringe 112 may be encased in a protective cover (not shown) to increase its rigidity and prevent contamination. The protective cover may or may not be removed from the rolling diaphragm syringe 112 prior to installation on the injector 102. The rolling diaphragm syringe 112 may be formed to have a variety of shapes. For example, the rolling diaphragm syringe 112 may be cylindrical, conical, spherical, ellipsoidal, egg-shaped, etc. Furthermore, the rolling diaphragm syringe 112 may have different width to length ratios. For example, the rolling diaphragm syringe 112 may be formed to have a diameter that is substantially smaller or larger compared to its longitudinal length. One of ordinary skill in the art will understand that the injector 102 may be desirably programmed to control the movement of the piston 138 in order to deliver a substantially constant and predictable flow rate of fluid from the rolling diaphragm syringe 112. In other aspects, the rolling diaphragm syringe 112 may be formed by a blow-stretch molding process from a preform, such as a process described in International patent application No. PCT/US2014/063477, filed Oct. 31, 2014, the disclosure of which is incorporated herein by this reference.

The outer diameter of the rolling diaphragm syringe 112 may be dimensioned such that the rolling diaphragm syringe 112 fits within the interior space defined by the throughbore and inner surface of the pressure jacket 110. In one aspect, the rolling diaphragm syringe 112 fits snuggly within the pressure jacket 110 such that the outer surface of the rolling diaphragm syringe 112 abuts the inner surface of the walls of the pressure jacket 110. In another aspect, the rolling diaphragm syringe 112 fits loosely within the pressure jacket 110 such that there is a gap between at least a portion of the outer surface of the rolling diaphragm syringe 112 and the inner surface of the pressure jacket 110. The rolling diaphragm syringe 112 may be expanded under pressure during an injection procedure such that the outer surface of the rolling diaphragm syringe 112 abuts the inner surface of the pressure jacket 110.

Figure 4A:
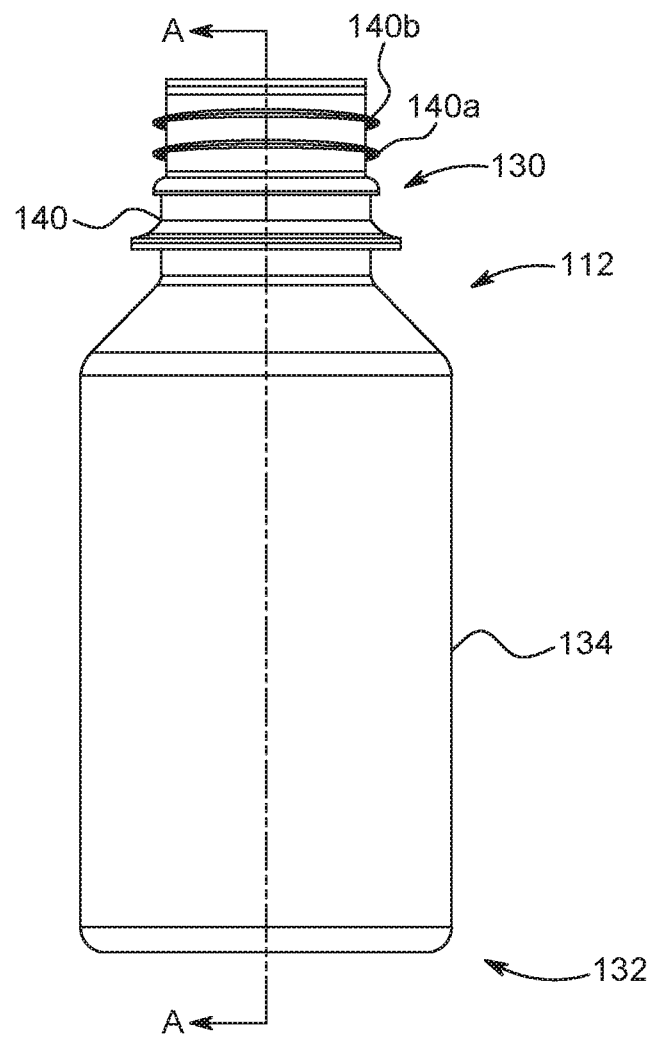
FIG. 4A is a side view a rolling diaphragm syringe in accordance with another aspect of the present disclosure.
Figure 4B:
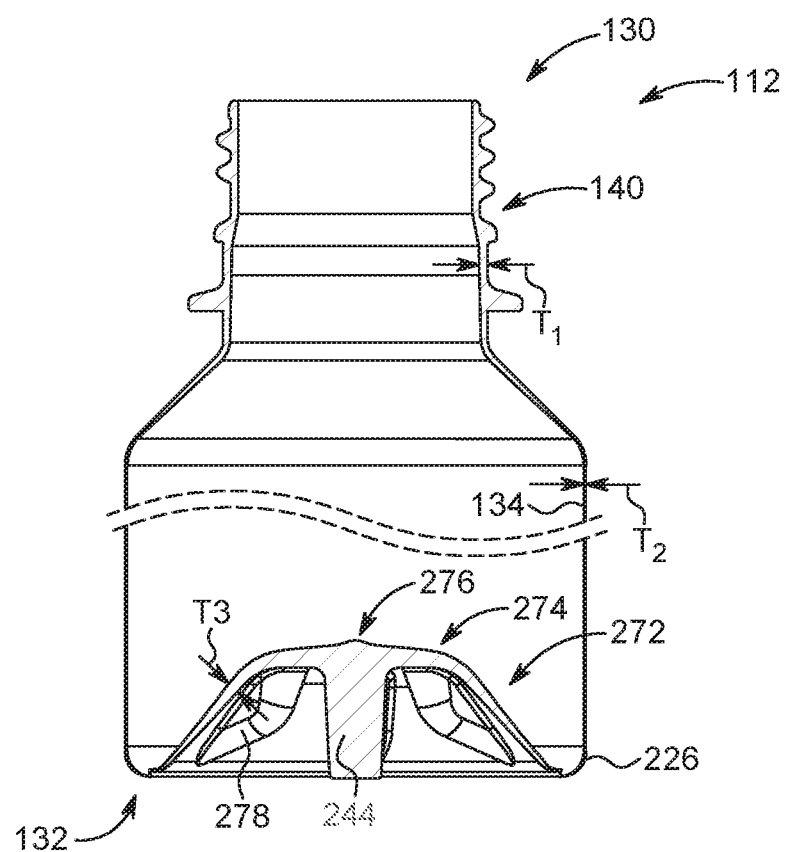
FIG. 4B is a cross-sectional side view the rolling diaphragm syringe shown in FIG. 4A taken along line A-A.

FIGS. 4A-4B show a rolling diaphragm syringe 112 in accordance with another aspect of the present disclosure. FIG. 4B is a cross-sectional side view the rolling diaphragm syringe 112 shown in FIG. 4A taken along line A-A. Many components of the rolling diaphragm syringe 112 shown in FIGS. 4A-4B are substantially similar to the components of the rolling diaphragm syringe 112 described herein with reference to FIGS. 2-3. Reference numerals in FIGS. 4A-4B are used to illustrate identical components as the corresponding reference numerals in FIGS. 2-3. As the previous discussion regarding the rolling diaphragm syringe 112 generally shown in FIGS. 2-3 is applicable to the aspect shown in FIGS. 4A-4B, only the relevant differences between these systems are discussed hereinafter.

Figure 5A:
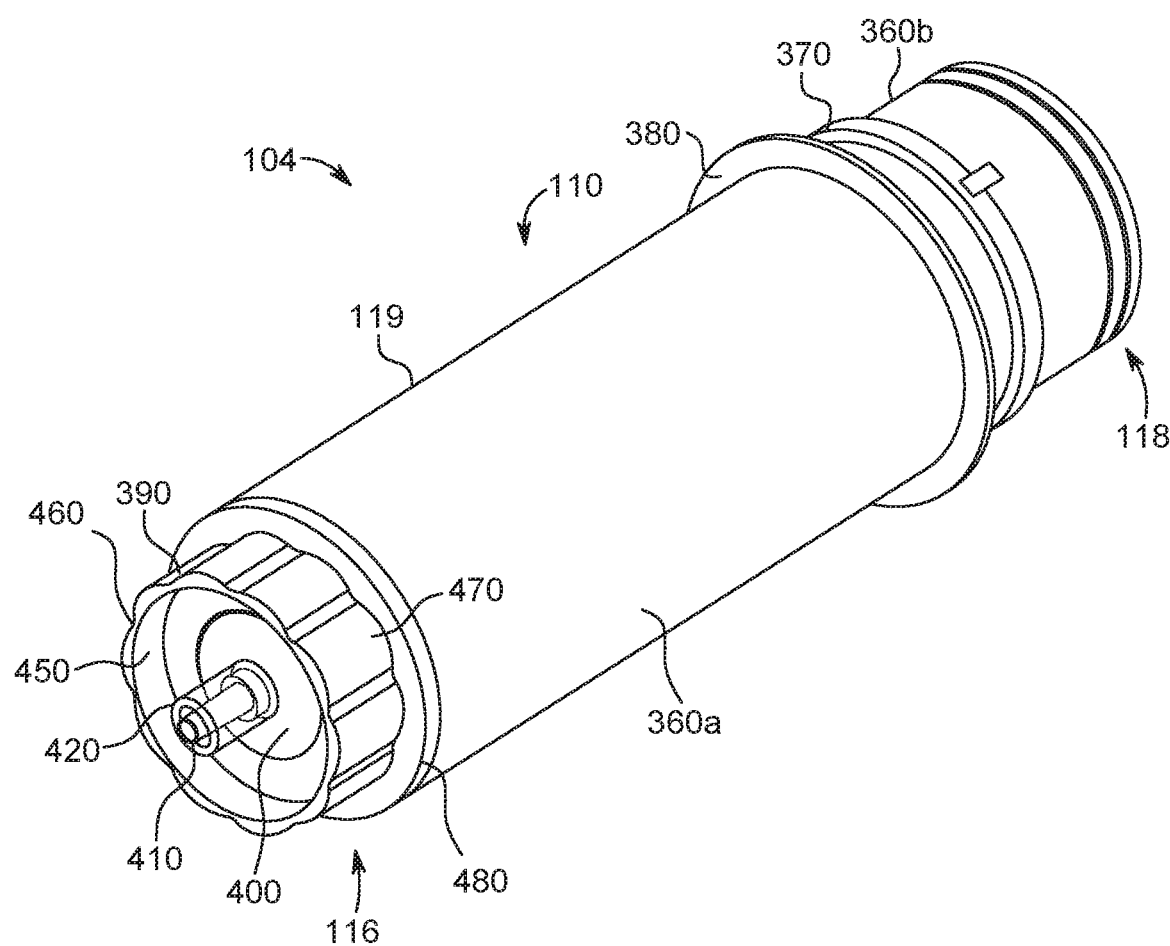
FIG. 5A is a perspective view of a rolling diaphragm syringe and a pressure jacket in accordance with another aspect of the present disclosure.
Figure 6:
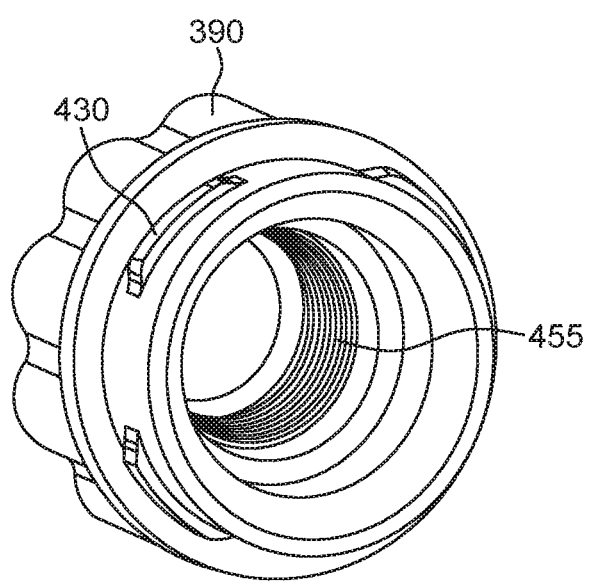
FIG. 6 is a bottom perspective view of the cap shown in FIG. 5C.

Referring initially to FIG. 4A, the distal end 130 of the rolling diaphragm syringe 112 has an open-ended discharge neck 140 having a connection member 140a for connecting to a corresponding connection member, for example the cap of FIG. 6 as described herein, which may connect to a fluid path set (not shown). In certain aspects of the blow molding process, the open-ended discharge neck may be configured to receive a stretching element to stretch a preform during a blow-stretch molding process. In some aspects, the connection member 140a is a threaded interface having one or more threads 140b for mating with corresponding threads 455 (see FIG. 6) on the connection member to the fluid path set. In certain aspects, the connection member 140a may be configured to connect to the fluid path, such as by way of luer-type connection. In other aspects, the connection member 140a may have one or more lips or grooves that interact with corresponding grooves or lips on a cap 390 of the pressure jacket 110 (shown in FIG. 5A) to releasably or non-releasably retain the rolling diaphragm syringe 112 with the cap 390 of the pressure jacket 110.

With reference to FIG. 4B, the discharge neck 140 has a first sidewall thickness $T_1$ that is greater than a thickness $T_2$ of the sidewall 134. Thickness $T_1$ is selected such that the discharge neck 140 may be sufficiently rigid to allow for connecting to a corresponding connection member of a fluid path set (not shown) without substantially deforming the discharge neck 140, for example during an injection procedure. Thickness $T_2$ is selected such that the sidewall 134 of the rolling diaphragm syringe 112 is flexible to allow for rolling over and unrolling of the sidewall 134 as described herein. The proximal end 132 of the rolling diaphragm syringe 112, such as the closed end wall 136, may be reinforced to prevent deformation during rolling over or in particular aspects, unrolling of the sidewall 134. In some aspects, the proximal end 132 of the rolling diaphragm syringe 112 is configured for engagement with the piston 138 (not shown) as described herein. The proximal end 132 has a radiused folding edge 226 configured to initiate the initial rolling over and in certain aspects, unrolling of the sidewall 134 of the rolling diaphragm syringe 112. The folding edge 226 may transition into a distally-extending ramp 272 having continuously increasing sidewall thickness $T_3$ to a distal portion 274 of the end wall 136. In some aspects, the sidewall thickness $T_3$ may be greater than sidewall thickness $T_2$ over at least a portion of the end wall 134. In various aspects, sidewall thickness $T_3$ may be between 0.01 inches-0.15 inches.

The end wall 134 may have a central portion 276 having a substantially dome-shaped structure and a piston engagement portion 244 extending proximally from the central portion 276, such as an approximate midpoint of the central portion 276. In some aspects, a distal most end of the central portion 276 may be substantially flat. The piston engagement portion 244 is configured for engagement with the engagement mechanism on the piston of the fluid injector 102, as described herein. The proximal end 132 of the rolling diaphragm syringe 112 may have one or more ribs 278 protruding radially outward from the piston engagement portion 244 along a proximal surface of the ramp 272.

FIG. 5A is a perspective view of a syringe assembly 104 having a rolling diaphragm syringe 112 (shown in FIG. 5B) and a pressure jacket 110 in accordance with another aspect of the present disclosure. The syringe assembly 104 includes the pressure jacket 110 that removably interfaces with the injector 102 (shown in FIG. 1), as described herein. The pressure jacket 110 has a distal end 116, a proximal end 118, and a sidewall 119 extending between the distal end 116 and the proximal end 118 along a longitudinal axis of the pressure jacket 110 to define an internal throughbore 121 (shown in FIG. 5B). In some aspects, the sidewall 119 of the pressure jacket 110 is shaped to receive at least a portion of the rolling diaphragm syringe 112 (shown in FIG. 5B) within the throughbore 121. For example, the sidewall 119 may be substantially cylindrical. The sidewall 119 of the pressure jacket 110 has a first distal portion 360a for receiving at least a portion of the rolling diaphragm syringe 112, and a second proximal portion 360b for interfacing with the injector 102. The first distal portion 360a may have an open end configured to releasably receive a cap 390 that encloses the interior of the pressure jacket 110. The second proximal portion 360b may have an open end to allow the piston 138 of the fluid injector 102 to extend through the open end and engage rolling diaphragm syringe 112 held within throughbore 121. The rolling diaphragm syringe 112 may be inserted through the open end of the first distal portion 360a or the second proximal portion 360b.

In some aspects, the second proximal portion 360b has a flange 380 protruding radially outward from an outer surface of the second proximal portion 360b. The flange 380 may extend continuously or discontinuously around an outer circumference of the second proximal portion 360b. Desirably, the flange 380 extends continuously around the entire outer circumference of the second proximal portion 360b. The flange 380 is configured for collecting any fluid that may drip from the nozzle 410 of the rolling diaphragm syringe 112 into the connection port of the fluid injector 102.

In some aspects, the second proximal portion 360b has a locking lug or lip 370 protruding radially outward from an outer surface of the second proximal portion 360b. The locking lug or lip 370 may extend continuously or discontinuously around an outer circumference of the second proximal portion 360b. The locking lug or lip 370 is configured for interacting with corresponding features on the fluid injector 102 to releasably lock the pressure jacket 110 with the fluid injector 102. In some aspects, the locking lug or lip 370 may have a connection member to releasably secure the pressure jacket 110 to a corresponding locking mechanism of the fluid injector 102 described in U.S. Pat. Nos. 5,383,858; 5,873,861; 6,652,489, 9,173,995; and 9,199,033. Other connection members between the pressure jacket 110 and the fluid injector 102 are described in International Application No. PCT/US2015/057751, filed Oct. 28, 2015, or International Application No. PCT/US2015/057747, filed Oct. 28, 2015.

Figure 5B:
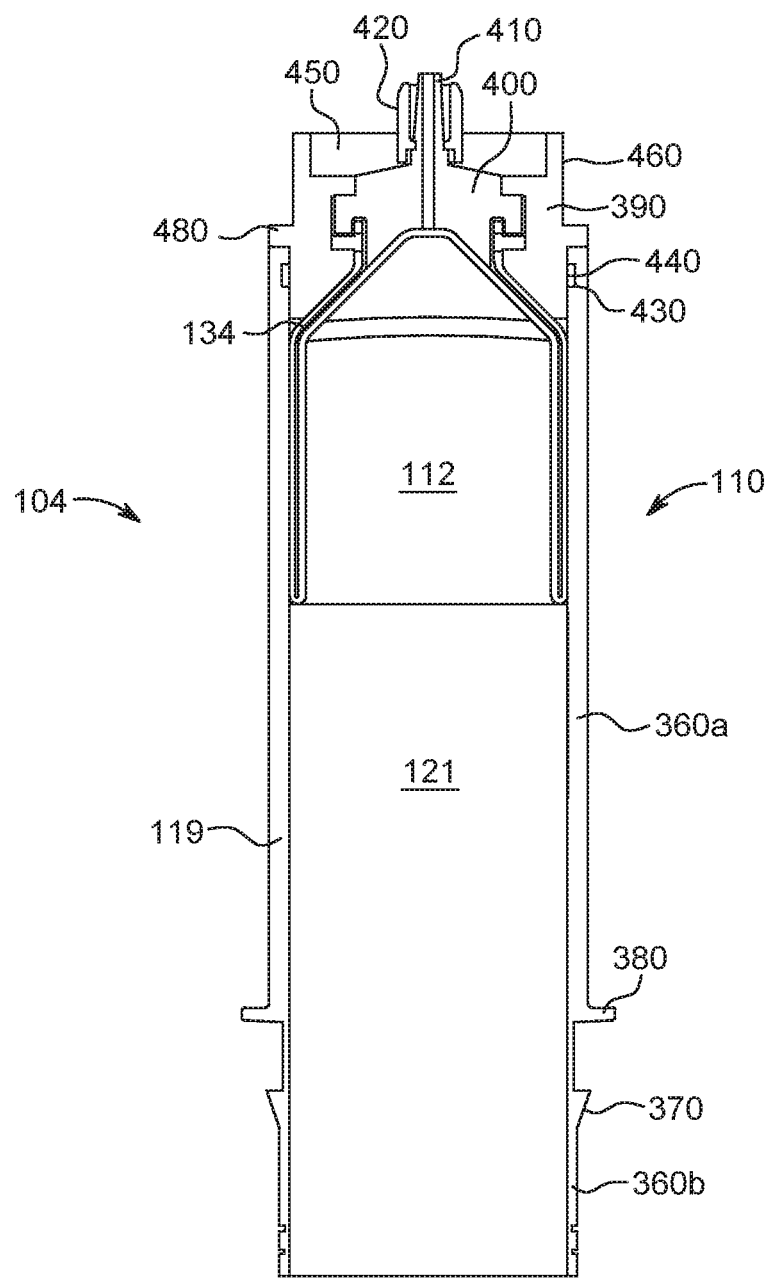
FIG. 5B is a cross-sectional side view of the rolling diaphragm syringe and the pressure jacket shown in FIG. 5A.

With reference to FIG. 5B and with continued reference to FIG. 5A, the pressure jacket 110 may have a cap 390 that is releasably secured to the distal end 116. In some aspects, the cap 390 may be secured by a threaded engagement, a bayonet fitting, or another mechanical fastening arrangement with the distal end 116 of the pressure jacket 110. For example, as shown in FIG. 5B, the cap 390 may have at least one projection 430 that is received inside at least one groove 440 on the pressure jacket 110 such that the cap 390 may be locked with the pressure jacket 110 by aligning the at least one projection 430 to fit within the groove 440. In some aspects, the cap 390 may be locked onto the pressure jacket 110 by rotating the cap 390 about its longitudinal axis relative to the pressure jacket 110, such as by rotating the cap 390 a portion of a full revolution in a first direction (clockwise or counterclockwise), until the at least one projection 430 is positioned within the groove 440 to prevent axial movement of the cap 390 relative to the pressure jacket 110. To unlock or disconnect the cap 390 from the pressure jacket 110, the cap 390 may be rotated in a second direction opposite to the first direction (counterclockwise or clockwise) to disengage the at least one projection 430 from the groove 440. In some aspects, the cap 390 may be formed from two or more separate elements that are joined together to form the cap 390, such as in a clam-shell type arrangement. For example, the cap 390 may have two elements joined together at a longitudinal cross-sectional plane of the cap 390. A retention ring may be provided around at least a portion of the separate elements to retain the elements of the cap 390 around and secured to the distal discharge neck 140 of rolling diaphragm syringe 112. The cap 390 may have an inner element 400 with a nozzle 410. The inner element 400 may be formed directly with the cap 390, or it may be formed separately and inserted into a central opening of the cap 390. The inner element 400 may be formed directly on the distal end of the rolling diaphragm syringe 112, such as on the distal discharge neck 140, and be inserted into the central opening of the cap 390. The nozzle 410 may be in fluid communication with the interior volume of the rolling diaphragm syringe 112 (or directly formed on the rolling diaphragm syringe 112) to deliver fluid into or from the rolling diaphragm syringe 112. The nozzle 410 may have a connection member 420 for removably connecting to a connector of the fluid path set 108 (shown in FIG. 1). For example, the connection member 420 may be an annular skirt that surrounds the nozzle 410 and has one or more engagement elements that engage the corresponding connector of the fluid path set 108. In some aspects, the connection member 420 or nozzle 410 may be a luer-type fitting.

The cap 390 may have a pocket 450 for collecting any fluid that may drip from the nozzle 410 and/or the connector 420. The pocket 450 is defined by an annular sidewall 460 that extends around the nozzle 410 and the connector 420. The annular sidewall 460 may have one or more gripping elements 470 to facilitate gripping of the cap 390 when the cap 390 is connected to and/or disconnected from the pressure jacket 110. In some aspects, the gripping elements 470 may protrude radially outward from at least a portion of the outer surface of the annular sidewall 460. The cap 390 may have a radial flange 480 that extends radially outward from a proximal portion of the annular sidewall 460. The radial flange 480 may extend continuously or discontinuously around an outer circumference of the cap 390. Desirably, the radial flange 480 extends continuously around the entire outer circumference of the cap 390. The radial flange 480 may have the same outer diameter as the pressure jacket 110 such that an outer radial surface of the radial flange 480 is flush with the diameter of the outer sidewall 119 of the pressure jacket 110.

Figure 5C:
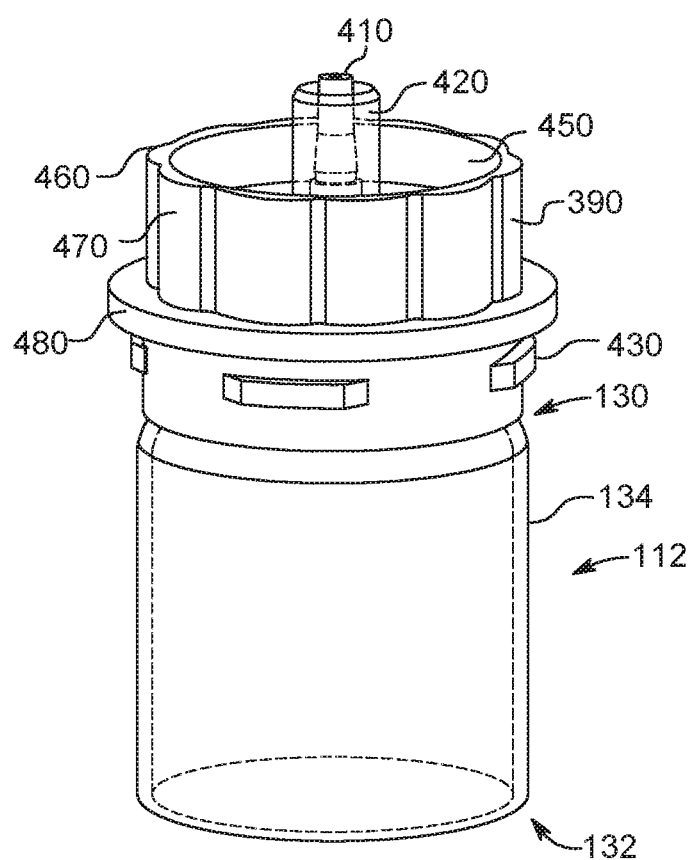
FIG. 5C is a perspective view of a rolling diaphragm syringe and a cap for use with the pressure jacket shown in FIG. 4A.

With reference to FIG. 5C, at least a portion of the rolling diaphragm syringe 112 may be removably secured to the cap 390. In some aspects, the cap 390 may have a connection member that corresponds to and connects with the connection member 140a (shown in FIG. 4A) of the rolling diaphragm syringe 112. For example, an inner sidewall of the cap 390 may have one or more threads 455 (shown in FIG. 6) that engage the corresponding threads 140b (shown in FIG. 4A) on the rolling diaphragm syringe 112. The one or more threads 455 may have a radial taper from a proximal end to a distal end such that the threads 455 engage the connection member 140a of the rolling diaphragm syringe 112 progressively tighter as the cap 390 is tightened to the discharge neck 140 of the rolling diaphragm syringe 112. In other aspects, the cap 390 may be secured to the rolling diaphragm syringe 112 by a snap-fit, clam-shell fit, interference fit, adhesive connection, co-molding, threaded fit, or any other mechanical fastening arrangement. For example, the cap 390 may be secured to the rolling diaphragm syringe 112 by interacting with one or more radial ribs and/or grooves extending around an outer circumference of the discharge neck 140 of the rolling diaphragm syringe 112. In some aspects, an O-ring seal may be provided at the connection interface between the cap 390 and the discharge neck 140 of the rolling diaphragm syringe 112. In other aspects, the rolling diaphragm syringe 112 may have a built-in cap 390. In various aspects, the rolling diaphragm syringe 112 may be removably or non-removably connected to the cap 390. Desirably, the rolling diaphragm syringe 112 is secured to the cap 390 prior to being inserted into the throughbore 121 of the pressure jacket 110. After securing the cap 390 to the pressure jacket 110, the piston 138 (shown in FIG. 2) may engage the rolling diaphragm syringe 112 to deliver fluid into or from the rolling diaphragm syringe 112, as described herein.

As further shown in FIG. 5C, the rolling diaphragm syringe 112 may initially be in a compressed configuration where the rolling diaphragm syringe 112 is rolled over on itself. Providing the rolling diaphragm syringe 112 in an initial compressed configuration may provide economic benefits during packaging and shipping by requiring less packaging material per syringe set up and/or allowing more syringe set-ups to be package. Further, the smaller size of the syringe in the compressed state requires less room for storage of syringe packs within the injection room or suite. Further, due to the use of less material in the design of the syringe sidewall, manufacturing costs are reduced due to the need for less raw materials and shipping costs are reduced due to reduced weight of the syringes and packaging materials.

Figure 7A:
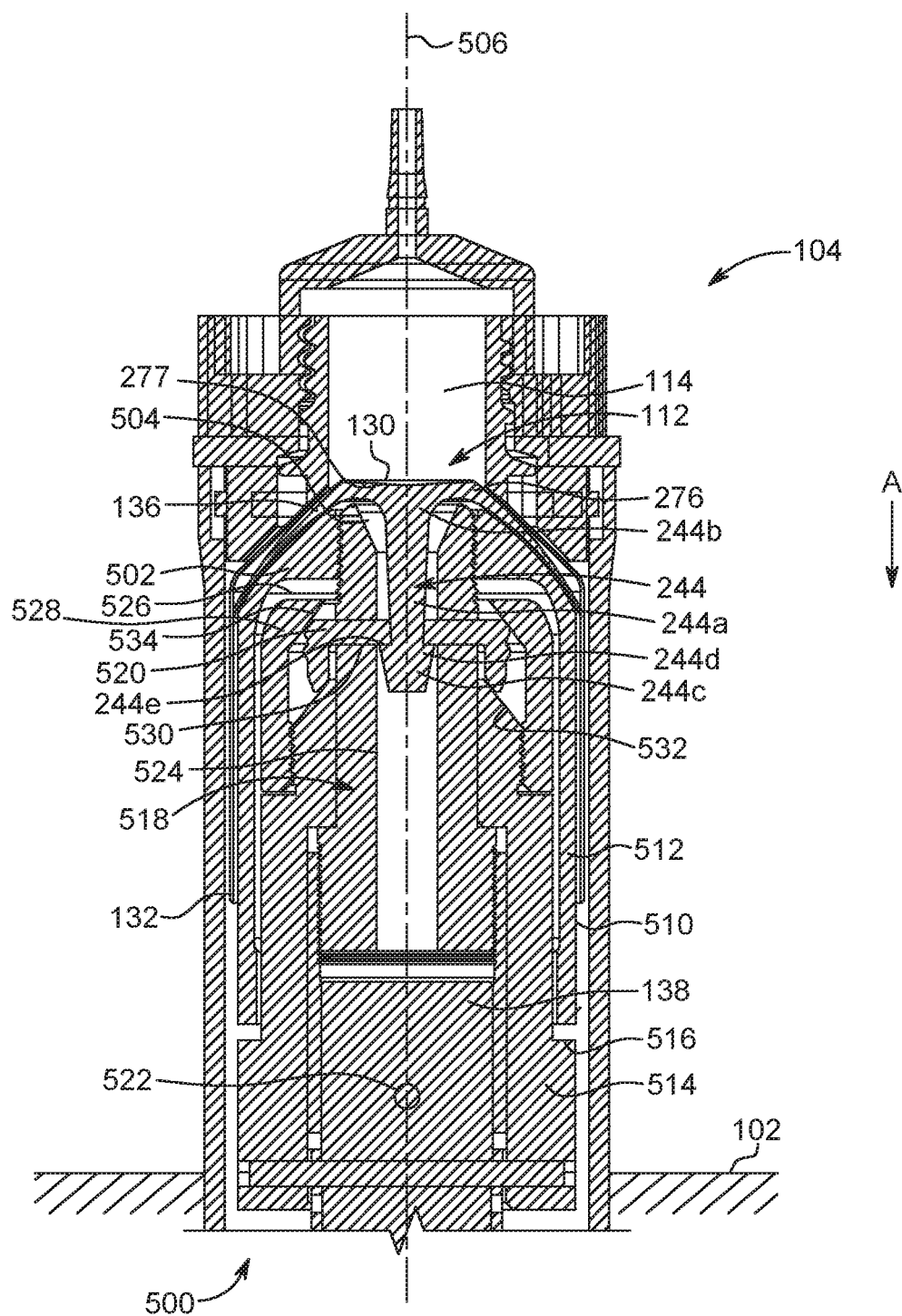
FIG. 7A is a cross-sectional view of a rolling diaphragm syringe, a pressure jacket, and an engagement mechanism for connecting a piston of a fluid injector to the rolling diaphragm syringe, with the engagement mechanism shown in a first state.
Figure 7B:
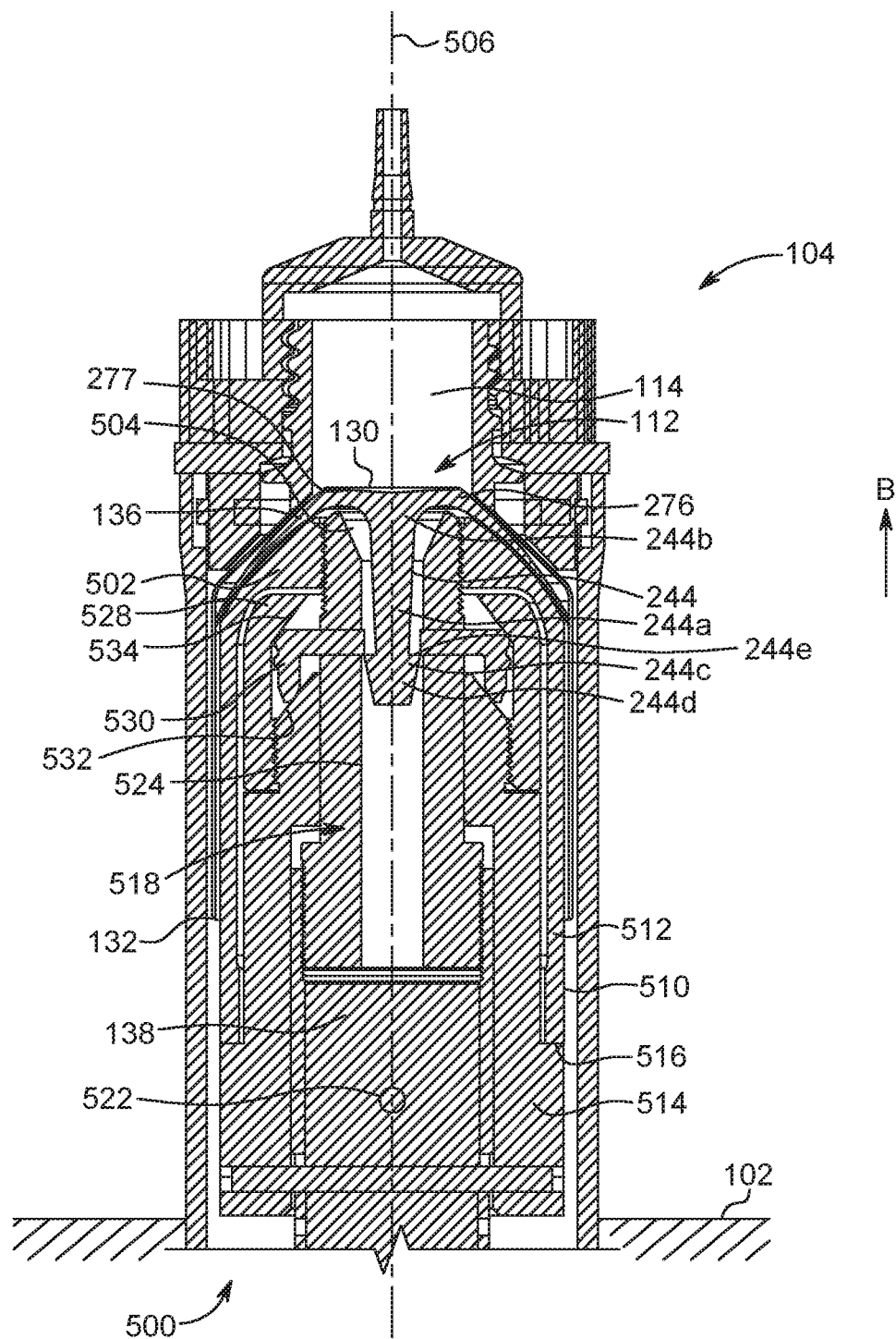
FIG. 7B is a cross-sectional view of the rolling diaphragm syringe, the pressure jacket, and the engagement mechanism of FIG. 7A, with the engagement mechanism shown in a second state.

With reference to FIGS. 7A-7B, the syringe assembly 104 is shown with an engagement mechanism 500 of the fluid injector 102 for engaging the piston 138 of the fluid injector 102 with the rolling diaphragm syringe 112 according to one aspect of the present disclosure. The rolling diaphragm syringe 112 in FIGS. 7A-7B is shown in an empty, compressed state where the interior volume of the rolling diaphragm syringe 112 is not filled with fluid, such as when an empty rolling diaphragm syringe 112 is initially inserted into the pressure jacket. In other aspects, the interior volume of the rolling diaphragm syringe 112 may be at least partially filled with fluid. The central portion 276 of the rolling diaphragm syringe 112 has a substantially dome-shaped structure and the piston engagement portion 244 extends proximally from the central portion 276. The piston engagement portion 244 is configured for engagement with the engagement mechanism 500 of the fluid injector 102. In some aspects, the piston engagement portion 244 has a stem 244a having a first end 244b connected at the central portion 276 and a second end 244c extending proximally from the first end 244b. In some aspects, a diameter of the stem 244a may be uniform between the first end 244b and second end 244c. In other aspects, the diameter of the stem 244a may be non-uniform between the first end 244b and the second end 244c. For example, the diameter of the stem 244a may gradually decrease from the first end 244b to the second end 244c.

The second end 244c has an engagement member, such as at least one flange or protrusion 244d, that protrudes radially outward relative to the diameter of the stem 244a. In some aspects, the engagement member may be configured as a lip (not shown) that is recessed radially inward into the stem 244a. The at least one protrusion 244d may extend circumferentially around at least a portion of the stem 244a in a continuous or discontinuous manner. In some aspects, the protrusion 244d may be monolithically formed with the stem 244a. In other aspects, the protrusion 244d may be formed separately from the stem 244a and removably or non-removably attached to the stem 244a. In one aspect, the engagement member protrusion 244d may be attached to the proximal end of stem 244a, for example by an adhesive or by a mechanical mechanism. For example, in one aspect the engagement member may be screwed into the proximal end of stem 244a wherein the screw head may form protrusion 244d. In other aspects, the protrusion 244d may be integrally formed with the stem 244a in one or multiple manufacturing steps, such as by molding the protrusion 244d together with the stem 244a, or molding the stem 244a first followed by a separate manufacturing process to form the protrusion 244d. In one aspect, the protrusion 244d may be formed by heating and rolling or compressing the second end 244c of the stem 244a after the stem 244a is molded. The protrusion 244d is configured for interacting with one or more engagement pins or surfaces of the engagement mechanism 500 that move radially inward and outward to engage and disengage, respectively, the stem 244 of the rolling diaphragm syringe 112 with the engagement mechanism 500 of the fluid injector 102. In some aspects, the protrusion 244d has a distally facing surface 244e configured to engage a proximal surface of the one or more engagement pins/surfaces 520, as described herein.

With continued reference to FIGS. 7A-7B, the piston 138 includes an outer piston section 510 having an outer piston sleeve 512 and an abutment section 514 attached thereto. The outer piston sleeve 512 has an outer engagement surface 502 for engaging at least a portion of the rolling diaphragm syringe 112. In some aspects, the outer engagement surface 502 of the piston 138 may contact at least a portion of the proximal end of the rolling diaphragm syringe 112, such as the end wall 136. The outer engagement surface 502 may be shaped to correspond to the shape of the end wall 136 such that the outer engagement surface 502 is in surface-to-surface contact with the end wall 136 of the rolling diaphragm syringe 112. Outer piston sleeve 512 forms a surface over which the side wall of rolling diaphragm syringe syringe 112 may roll over during a filling or dispensing process by reciprocal movement of the piston.

The abutment section 514 is axially movable relative to the outer piston section 510. Abutment of a distally facing flange or ledge 516 of the abutment section 514 with a proximal surface of the outer piston sleeve 512 causes the piston 138 to move distally relative to the rolling diaphragm syringe 112 to expel fluid from the interior volume of the rolling diaphragm syringe 112. The abutment section 514 is movable or slidable in an axial direction relative to the outer piston section 510 to control the state or position of one or more engagement pins or surfaces 520. The motion of the abutment section 514 relative to the outer piston section 510 is limited to allow engagement or disengagement of the pins/surfaces 520 with engagement member protrusion 244d. For example, such relative motion can be limited using a pin 522 fixed to abutment section 514. The pin 522 passes through and seats within a slot formed in the outer piston sleeve 510. In some aspects, the abutment section 514 may be movable by about 0.100 to 0.150 inches, for example 0.125 inches, before the outer piston section 510 is moved together with the abutment section 514.

The piston 138 also has an inner piston section 518 having a central opening 524. The central opening 524 of the inner piston section 518 is concentric with an opening 504 that extends through a central portion of the outer piston section 510 along a longitudinal axis 506 of the piston 138. The central opening 524 of the inner piston section 518 and the opening 504 of the outer piston section 510 are shaped to receive the piston engagement portion 244 of the rolling diaphragm syringe 112. Desirably, an inner diameter of the openings 504, 524 is slightly larger than an outer diameter of the widest portion of the piston engagement portion 244 to allow free insertion of the piston engagement portion 244 into the openings 504, 524. In certain aspects, diameter of the opening 504 is conical to guide engagement portion 244 into the correct position for engagement or disengagement of the pins/surfaces 520 with engagement member protrusion 244d.

With continued reference to FIGS. 7A-7B, the one or more engagement pins/surfaces 520 are positioned inside a pocket 526 defined between the abutment section 514 and a clamping ring 528. The clamping ring 528 is removably attached to the abutment section 514, such as by a threaded connection. The one or more engagement pins/surfaces 520 are configured to extend and retract in a radial direction through passages 530 due to movement of the abutment section 514 relative to the inner piston section 518. The passages 530 restrict axial movement of the one or more engagement pins 520 relative to the inner piston section 518 but allow radial movement. The one or more engagement pins/surfaces 520 are substantially L-shaped and are configured to contact one of the abutment section 514 or the clamping ring 528 depending on whether the piston 138 is moved in proximal direction A or distal direction B. Such contact with one of the abutment section 514 or the clamping ring 528 causes the one or more pins/surfaces 520 to be extended from or retracted into the passages 530.

The radial extension and retraction of the one or more engagement pins/surfaces 520 is controlled by engagement with at least a portion of the clamping ring 528 during proximal movement of the piston 138 and at least a portion of the abutment section 514 during distal movement of the piston 138, respectively. The abutment section 514 has an opening ramp 532 while the clamping ring 528 has a closing ramp 534. The opening and closing ramps 532, 534 are surfaces that are angled relative to the longitudinal axis 506 such that movement of the abutment section 514 relative to the inner piston section 518 urges the one or more pins/surfaces 520 to contact one of the ramps 532, 534 and effect radially inward or outward movement of the one or more pins/surfaces 520. During movement of the piston 138 in the proximal direction, such as shown by arrow A in FIG. 7A, the one or more engagement pins/surfaces 520 contact the closing ramp 534 on the clamping ring 528, thereby causing the one or more engagement pins 520 to slide along the closing ramp 534 and radially extend inward towards the longitudinal axis 506 through the passages 530. As the one or more engagement pins/surfaces 520 extend radially inward into the central opening 524 of the inner piston section 518, the one or more engagement pins/surfaces 520 are positioned distally of the distal surface 244e of the protrusion 244d of the piston engagement portion 244. During further proximal movement of the piston 138, a proximal surface of the one or more engagement pins/surfaces 520 contacts the protrusion 244d and pulls the piston engagement portion 244 of the rolling diaphragm syringe 112 in the proximal direction. Because the piston engagement portion 244 is integrally formed with the sidewall 134 of the rolling diaphragm syringe 112, the sidewall 134 is rolled out from being inverted upon itself to allow filling of interior volume 114 of the rolling diaphragm syringe 112 with fluid. In this manner, if the interior volume 114 of the rolling diaphragm syringe 112 is initially empty (or partially filled) and the proximal end 132 of the rolling diaphragm syringe 112 is rolled upon itself toward the distal end 130, the rolling diaphragm syringe 112 can be unrolled and withdrawn in the proximal direction by the piston 138 to fill the interior volume 114 with fluid. In order to prevent the end wall 136 from rolling upon itself before the sidewall 134 starts rolling upon itself, the end wall 136 desirably has a thicker sidewall relative to a thickness of the sidewall 134, as discussed herein.

Fluid can be delivered from the interior volume 114 of the rolling diaphragm syringe 112 by driving the piston 138 in the distal direction. During movement of the piston 138 in the proximal direction, such as shown by arrow B in FIG. 7B, the one or more engagement pins 520 contact the opening ramp 532 on the abutment section 514, thereby causing the one or more engagement pins/surfaces 520 to slide along the opening ramp 532 and radially retract away from the longitudinal axis 506. As the one or more engagement pins/surfaces 520 are radially retracted from the central opening 524 of the inner piston section 518, the one or more engagement pins/surfaces 520 come out of contact with the protrusion 244d of the piston engagement portion 244 and the outer piston section 510 pushes the proximal end 132 of the rolling diaphragm syringe 112 in the distal direction. The sidewall 134 of the rolling diaphragm syringe 112 is inverted upon itself, thereby reducing the interior volume 114 of the rolling diaphragm syringe 112 to deliver fluid from the rolling diaphragm syringe 112. In this manner, if the interior volume 114 of the rolling diaphragm syringe 112 is fully or partially filled, the rolling diaphragm syringe 112 can be rolled by folding the sidewall 134 of the rolling diaphragm syringe 112 upon itself due to distal movement of the piston 138 to deliver fluid from the interior volume 114. The rolling diaphragm syringe 112 can be refilled with fluid once some or all of the fluid has been discharged from the interior volume 114 by retracting the piston 138 in the proximal direction A, as described herein.

Figure 8:
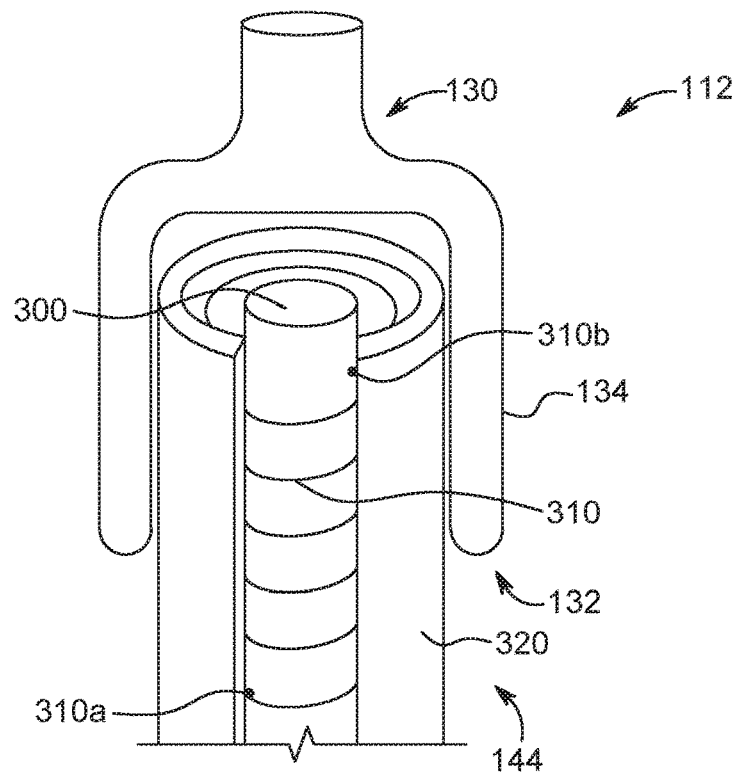
FIG. 8 is a side cross-sectional view of a rolling diaphragm syringe and a plunger in accordance with another aspect of the present disclosure.

FIG. 8 is a cross-sectional side view of a rolling diaphragm syringe 112 and a plunger 144 in accordance with another aspect of the present disclosure. The plunger 144 has an inner element 300 and an elastic element 310 wrapped around at least a portion of the inner element 300. One end of the elastic element 310, such as a proximal end 310a or a distal end 310b, may be secured to the inner element 300, while the opposing end of the elastic element 310 is free to rotate about the inner element 300. Upon rotation of one end of the elastic element 310 around the inner element 300 in a first direction, such as a clockwise or a counterclockwise direction, the elastic element 310 may be expanded radially outward to engage an inner surface of an outer element 320 that surrounds the inner element 300 and the elastic element 310. The outer element 320 may be formed as a split cylinder with a slit extending along its longitudinal axis. An outer surface of the outer element 320 engages the sidewall 134 of the rolling diaphragm syringe 112. Thus, as the elastic element 310 expands against the inner surface of the outer element 320, the outer element 320 expands radially outward such that its outer surface engages the sidewall 134 of the rolling diaphragm syringe 112. In this manner, the plunger 144 may move the sidewall 134 of the rolling diaphragm syringe 112 to withdraw fluid or expel fluid from the interior volume 114 of the rolling diaphragm syringe 112. In some aspects, the elastic element 310, in the expanded state, may engage the sidewall 134 of the rolling diaphragm syringe 112. Upon rotation of the elastic element 310 around the inner element 300 in a second direction opposite the first direction, the elastic element 310 may contract radially inward, thereby disengaging the outer element 320. In some aspects, the elastic element 310, in the contracted state, may disengage from the sidewall 134 of the rolling diaphragm syringe 112.

Figure 9:
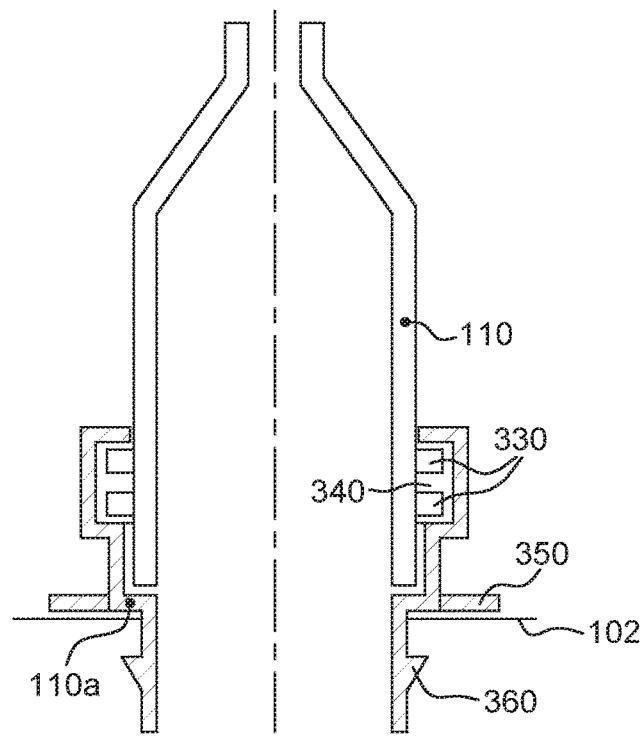
FIG. 9 is a side cross-sectional view of an adapter for a pressure jacket in accordance with another aspect of the present disclosure.

FIG. 9 is a cross-sectional side view of a pressure jacket 110 in accordance with another aspect of the present disclosure. The pressure jacket 110 may have an adapter 110a for releasably connecting the pressure jacket 110 with the injector 102. An outer sidewall of the pressure jacket 110 has one or more tabs 330 that protrude radially outward relative to the outer sidewall. The one or more tabs 330 are received in corresponding slots 340 of an engagement mechanism formed on the adapter 110a. In some aspects, the pressure jacket 110 may be secured to the adapter 110a by inserting the pressure jacket 110 into a central opening on the adapter 110a and rotating the pressure jacket 110 relative to the adapter 110a in a first direction (such as a partial turn in a clockwise or a counterclockwise direction) until the tabs 330 are received within the slots 340. Once received, the tabs 330 axially retain the pressure jacket 110 locked with the adapter 110a until the pressure jacket 110 is rotated in a second direction opposite the first direction (such as a partial turn in a counterclockwise or a clockwise direction). The adapter 110a may have a radial flange 350 protruding from an outer sidewall to prevent fluid from dripping into the injector 102. One or more locking elements 360 may be provided on the adapter 110a to removably lock the adapter 110a with a corresponding locking mechanism on the injector 102. In some aspects, the adapter 110a may be removably locked with the injector 102, such as by a bayonet connection. In other aspects, the adapter 110a may have a connection member to releasably secure the adapter 110a and the pressure jacket 110 to the fluid injector 102 in the form of a connection member described in U.S. Pat. Nos. 5,383,858; 5,873,861; 6,652,489, 9,173,995; or 9,199,033 discussed herein.

Figure 11A:
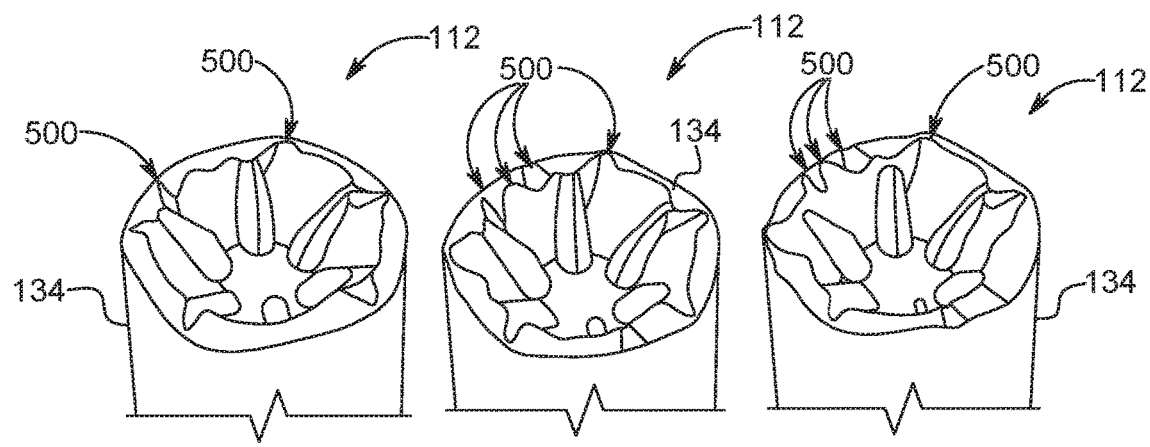
FIG. 11A is a perspective view of rolling characteristics of a rolling diaphragm syringe in accordance with another aspect.
Figure 11B:
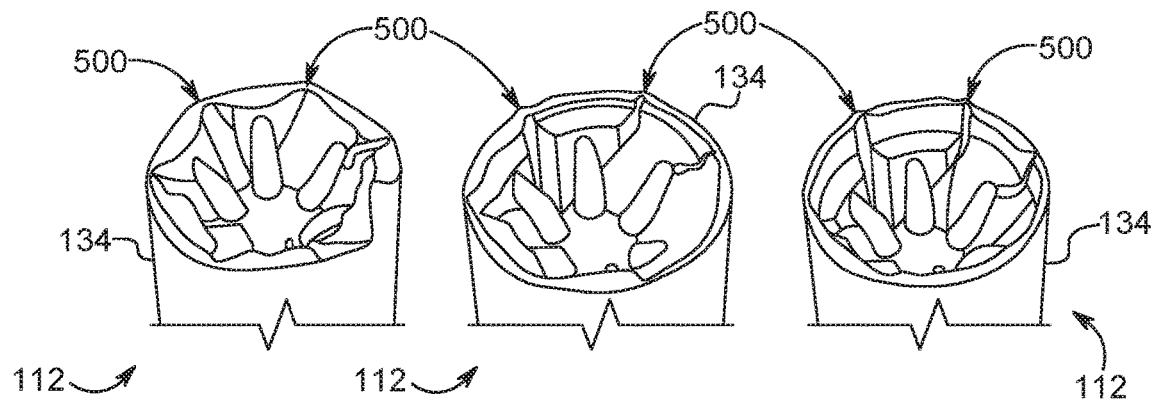
FIG. 11B is a perspective view of rolling characteristics of a rolling diaphragm syringe in accordance with another aspect.

A force that the plunger 144 needs to exert on the proximal end wall 132 of the rolling diaphragm syringe 112 to withdraw the end wall 132 in a controlled manner without longitudinal bending or pleating of the sidewall 134 of the rolling diaphragm syringe 112 is a function of one or more material properties of the rolling diaphragm syringe 112, such as Young's modulus of elasticity, thickness of the sidewall 134 at a folding region, frictional force between the plunger 144 and the inwardly facing outer sidewall of the rolling diaphragm syringe 112, and a diameter of the plunger 144 relative to a diameter of the rolling diaphragm syringe 112. In certain cases, during the rolling or unrolling of the sidewall 134, such as during a fluid filling or delivery procedure, one or more folds 500 may be developed at or near the rolled portion of the sidewall 134, which may result in error or inaccuracy in the volume of fluid drawing into or delivered from the rolling diaphragm syringe 112. With reference to FIGS. 11A-11B, one or more folds 500 are shown on the sidewall 134 of the rolling diaphragm syringe 112 during various stages of rolling over of the sidewall 134 when the correct wall thickness at the end portion and side walls is not used. This folding behavior, known as "pleating", may be caused by diameter reduction of the rolling diaphragm syringe 112 when an outer portion of the sidewall 134 is rolled upon itself. In certain cases, the pleating behavior may be exacerbated by non-uniform circumferential sidewall thickness, non-uniform geometry in the base, and/or localized contact between the plunger and the base. Once formed, the presence of the folds 500 is often maintained in the sidewall 134 during retraction of the plunger 144. Repeated filling and emptying of the rolling diaphragm syringe 112 may lead to an increase in localized material stresses in the sidewall 134 at the location of the folds 500. Further, folds 500 in sidewall 134 may affect accuracy of fluid delivery volume. Therefore, the material properties of the rolling diaphragm syringe 112, thickness of the sidewall 134 at a folding region, frictional force between the plunger 144 and the inwardly facing outer sidewall of rolling diaphragm syringe 112, and a diameter of the plunger 144 relative to a diameter of the rolling diaphragm syringe 112 are important design criteria when designing a fluid delivery system utilizing the rolling diaphragm syringe 112 in order to reduce or eliminate the formation and propagation of the folds 500 and allow for consistency and accuracy of fluid delivery.

Figures 10A, 10B:
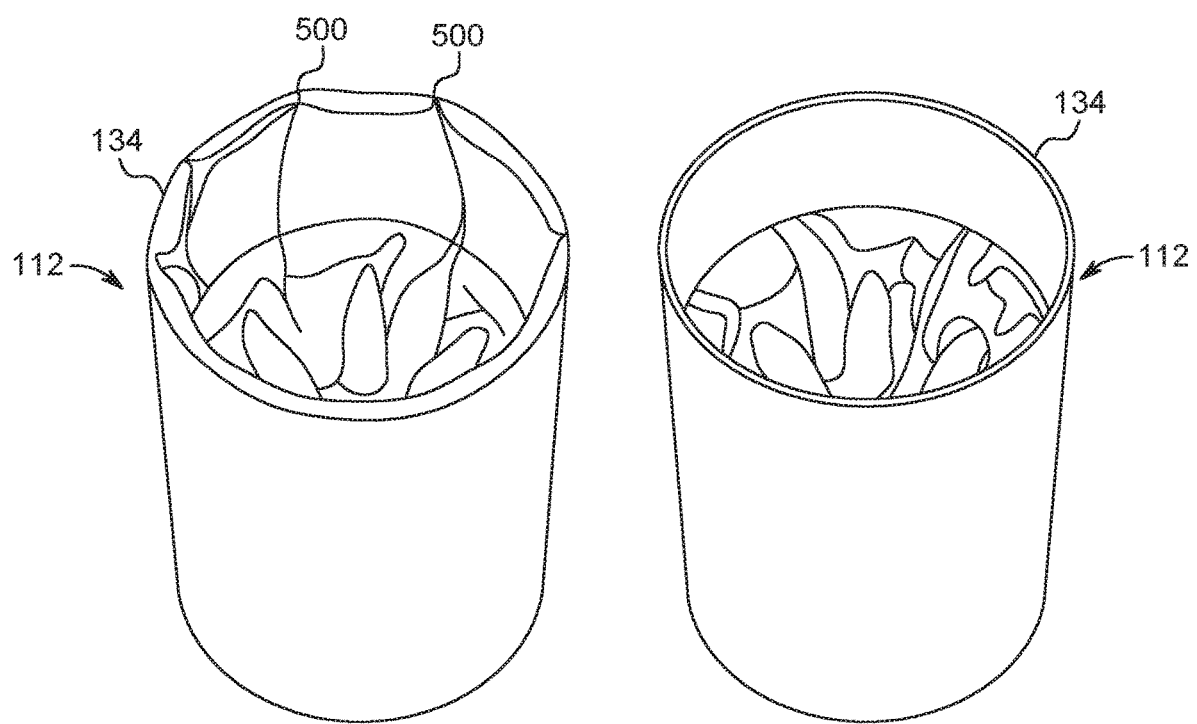
FIG. 10A is a perspective view of rolling characteristics of a rolling diaphragm syringe having a first diameter.
FIG. 10B is a perspective view of rolling characteristics of a rolling diaphragm syringe having a second diameter different from the first diameter of the rolling diaphragm syringe shown in FIG. 10A.
Figure 12A:
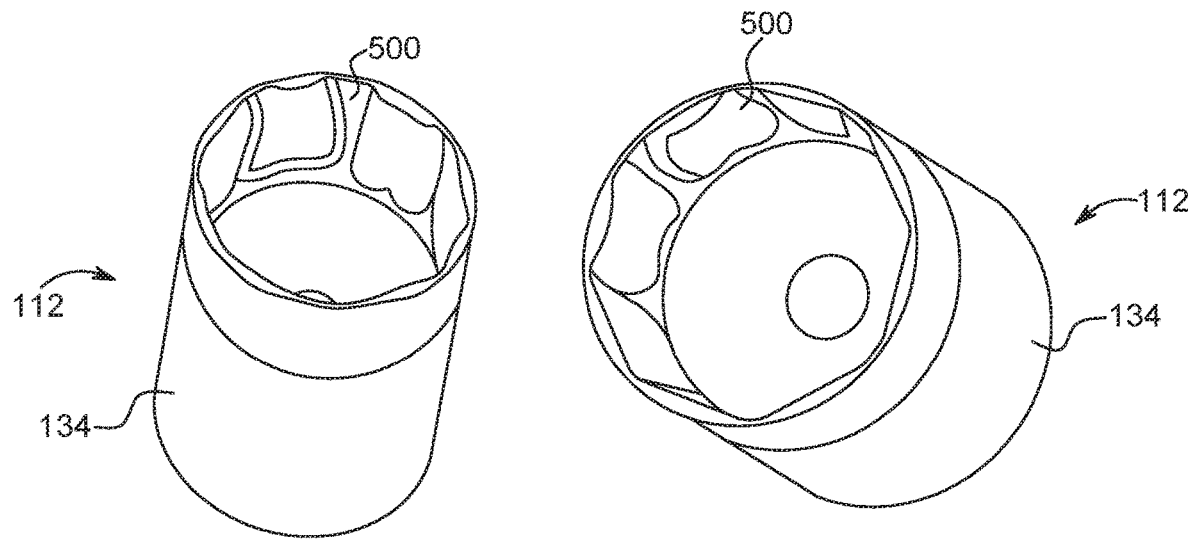
FIG. 12A is a perspective view of rolling characteristics of a rolling diaphragm syringe in accordance with another aspect.
Figure 12B:
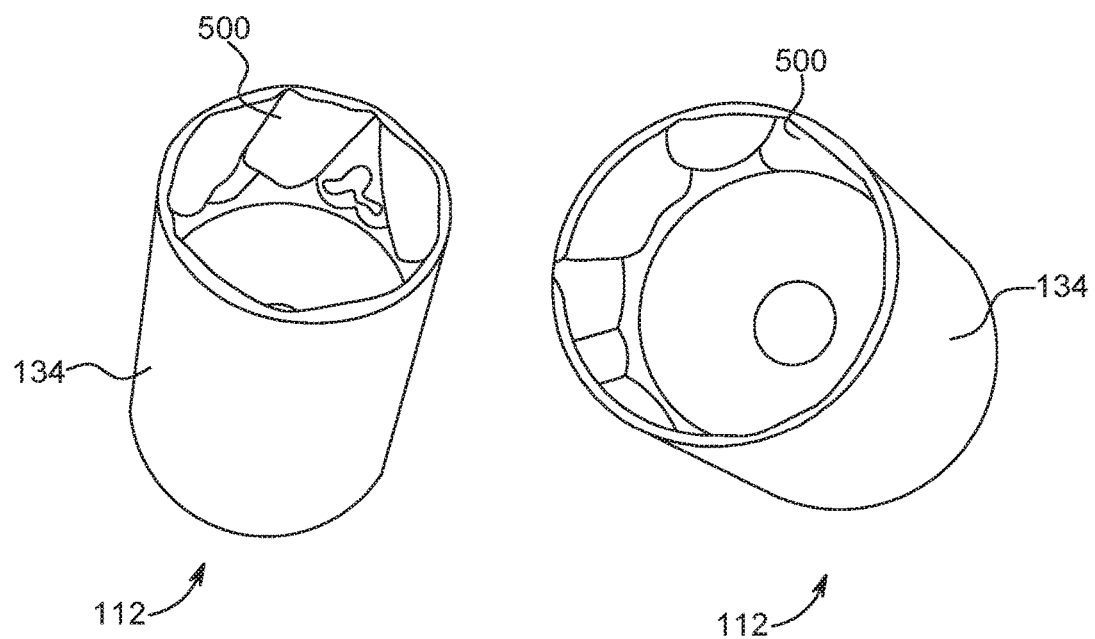
FIG. 12B is a perspective view of rolling characteristics of a rolling diaphragm syringe in accordance with another aspect.

In some aspects, pleating can be reduced or eliminated by controlling the plunger outer diameter relative to the outer diameter of the rolling diaphragm syringe 112 for a rolling diaphragm syringe 112 of a given material and sidewall thickness. In one test analysis, a first rolling diaphragm syringe 112 made from a PET material and having a sidewall thickness of 0.006" with a 1.805" outer diameter was rolled using a plunger 144 having an outer diameter of 1.609" (FIG. 10A), while a second rolling diaphragm syringe 112 made from the PET material and having a sidewall thickness of 0.006" with a 1.805" outer diameter was rolled using a plunger 144 having an outer diameter of 1.744" (FIG. 10B). With reference to FIG. 10A, in the first example pleating was manifested in the formation of the undesirable folds 500. In this example, a ratio of plunger diameter to rolling diaphragm syringe diameter was 0.891, with a 44 lb force necessary to drive the plunger 144. In other examples, ratios of plunger diameter to rolling diaphragm syringe diameter ranging from 0.892 to 0.999, in other aspects from 0.920 to 0.985, in still other aspects from 0.955 to 0.980, and still other aspects from 0.960 to 0.975 have been found to reduce or eliminate pleating of the sidewall 134. Pleating effects have been found to worsen as the plunger diameter is further reduced. With reference to FIG. 10B, pleating on the sidewall 134 of the rolling diaphragm syringe 112 is eliminated. In this aspect, the ratio of plunger diameter to rolling diaphragm syringe diameter is 0.966, with a 75 lb force necessary to drive the plunger 144. With reference to FIGS. 12A-12B, the pleating effect is reduced by doubling the sidewall thickness from 0.006 inch to 0.012 inch, for example from 0.008-0.015 inches. The plunger force is increased from 42 lbs to 208 lbs to initiate and maintain the rolling of the sidewall 134. Table I below includes test data for rolling diaphragm syringes 112 of various sidewall thicknesses used with plungers 144 of various diameters. Plunger force values ("Peak Rolling Force") are shown for each experimental example.

TABLE I

Syringe Diameter 1.804 in.
Pressure Jacket 1.845 in

| Data Set | Plunger Diameter in. | Syringe Design Name | Wall Thickness in. | Analysis Internal Pressure psi | SPECIFY Test Pressure psi | Peak Rolling Force (at FEA Pressure) lbf | Peak Rolling Force (without pressure contribution) lbf | Peak Rolling Force (at test Pressure) lbf | Pleating Y/N | Peak Rolling Force (based on Test data) lbf |
|---|---|---|---|---|---|---|---|---|---|---|
| Set 1 | 1.609 | C7668ES2 B | 0.006 | 80 | 7 | 248.29 | 43.74 | 61.64 | Y | |
|  | 1.744 | C7668ES2 B | 0.006 | 80 | 7 | 279.93 | 75.39 | 93.29 | N | |
| Set 2 | 1.609 | C7668ES4 A | 0.006 | 80 | 7 | 246.27 | 41.72 | 59.62 | Y | |
|  | 1.609 | C7668ES4 A | 0.012 | 80 | 7 | 412.18 | 207.63 | 225.53 | Y | |

TABLE I-continued

Syringe Diameter 1.804 in.
Pressure Jacket 1.845 in

| Data Set | Plunger Diameter in. | Syringe Design Name | Wall Thickness in. | Analysis Internal Pressure psi | SPECIFY Test Pressure psi | Peak Rolling Force (at FEA Pressure) lbf | Peak Rolling Force (without pressure contribution) lbf | Peak Rolling Force (at test Pressure) lbf | Pleating Y/N | Peak Rolling Force (based on Test data) lbf |
|---|---|---|---|---|---|---|---|---|---|---|
|  | 1.609 | C7668ES4 A | 0.012 | 80 | 7 | 435.56 | 231.01 | 248.91 | N |  |
|  | 1.744 | C7668ES4 A | 0.006 | 80 | 7 | 274.79 | 70.24 | 88.14 | N |  |
| Set 3 | 1.729 | C7668ES4 A | 0.006 | 80 | 7 | 264.20 | 59.66 | 77.56 | N | ~63 |
|  | 1.729 | C7668ES4 A | 0.008 | 80 | 7 | 326.45 | 121.90 | 139.80 | N |  |
|  | 1.729 | C7668ES4 A | 0.010 | 80 | 7 | 417.38 | 212.83 | 230.73 | N |  |
|  | 1.729 | C7668ES4 A | 0.012 | 80 | 7 | 550.63 | 346.09 | 363.98 | N |  |

While aspects of a fluid delivery system and a syringe for use therefor were provided in the foregoing description, those skilled in the art may make modifications and alterations to these aspects without departing from the scope and spirit of the disclosure. Accordingly, the foregoing description is intended to be illustrative rather than restrictive. The disclosure described hereinabove is defined by the appended claims and all changes to the disclosure that fall within the meaning and the range of equivalency of the claims are to be embraced within their scope.

We claim:

1. A rolling diaphragm syringe for receiving a medical fluid therein, the rolling diaphragm syringe comprising:
a proximal end comprising a concave end wall for engagement with a piston of a fluid injector, the proximal end comprising a radiused folding edge and wherein at least a portion of the concave end wall has non-uniform thickness;
a distal end having an open-ended discharge neck;
a sidewall extending between the proximal end and the distal end along a longitudinal axis; and
a piston engagement portion protruding proximally from a central portion of the concave end wall and configured for engagement with the piston of the fluid injector, wherein the piston engagement portion has a stem with a first end attached to the concave end wall and a second end extending proximally from the first end,
wherein the sidewall is flexible and rolls upon itself when acted upon by the piston such that an outer surface of the sidewall is folded in a radially inward direction as the piston is advanced from the proximal end to the distal end.

2. The rolling diaphragm syringe of claim 1, wherein the outer surface of the sidewall is unfolded in a radially outward direction as the piston is retracted from the distal end to the proximal end.

3. The rolling diaphragm syringe of claim 1, wherein at least a portion of the concave end wall continuously increases in thickness in a radially inward direction from the radiused folding edge.

4. The rolling diaphragm syringe of claim 1, wherein the discharge neck has a connection member for connecting to a cap.

5. The rolling diaphragm syringe of claim 1, further comprising at least one engagement member at the second end of the stem, wherein the at least one engagement member protrudes radially outward or radially inward relative to an outer surface of the stem and has a distal surface configured for engaging one or more engagement pins of the piston during movement of the piston in a proximal direction.

6. The rolling diaphragm syringe of claim 5, wherein the at least one engagement member is monolithically formed with the second end of the stem.

7. The rolling diaphragm syringe of claim 1, wherein the rolling diaphragm syringe is initially in a compressed, rolled state and is configured to be unrolled during a filling process as the piston retracts the concave end wall in a proximal direction.

8. A syringe assembly for a fluid delivery system, the syringe assembly comprising:
a pressure jacket having an open distal end, an open proximal end, and a sidewall with a throughbore extending between the open distal end and the open proximal end;
a rolling diaphragm syringe configured to be received within the throughbore of the pressure jacket, the rolling diaphragm syringe comprising:
a proximal end comprising a concave end wall for engagement with a piston of a fluid injector, the proximal end comprising a radiused folding edge and wherein at least a portion of the concave end wall has non-uniform thickness;
a distal end having an open-ended discharge neck;
a sidewall extending between the proximal end and the distal end along a longitudinal axis, wherein the sidewall of the rolling diaphragm syringe defines an interior volume for receiving a medical fluid therein; and
a piston engagement portion protruding proximally from a central portion of the concave end wall and configured for engagement with the piston of the fluid injector, wherein the piston engagement portion has a stem with a first end attached to the concave end wall and a second end extending proximally from the first end; and
a cap configured for engaging at least one of the distal end of the pressure jacket and the distal end of the rolling diaphragm syringe to enclose the open-ended discharge neck of the rolling diaphragm syringe,
wherein the sidewall of the rolling diaphragm syringe is flexible and rolls upon itself when acted upon by the piston such that an outer surface of the sidewall is folded in a radially inward direction as the piston is advanced from the proximal end of the rolling diaphragm syringe to the distal end of the rolling diaphragm syringe.

9. The syringe assembly of claim 8, wherein the proximal end of the pressure jacket has at least one locking lip or lug protruding radially outward from an outer surface of the sidewall of the pressure jacket for releasably locking the pressure jacket with the fluid injector.

10. The syringe assembly of claim 8, wherein the cap has at least one projection or groove that interacts with a corresponding groove or projection on the distal end of the pressure jacket for releasably securing the cap to the pressure jacket.

11. The syringe assembly of claim 8, wherein the cap has a nozzle and an annular sidewall surrounding the nozzle, the annular sidewall having one or more gripping elements protruding radially outward from an outer surface of the annular sidewall.

12. The syringe assembly of claim 8, wherein the cap is non-removably secured to the discharge neck of the rolling diaphragm syringe and wherein the cap has an engagement element for removably connecting the cap with the distal end of the pressure jacket.

13. The syringe assembly of claim 12, and wherein the outer surface of the sidewall is unfolded in a radially outward direction as the piston is retracted from the distal end of the rolling diaphragm syringe to the proximal end of the rolling diaphragm syringe.

14. The syringe assembly of claim 8, further comprising at least one engagement member at the second end of the stem, wherein the at least one engagement member of the piston engagement portion protrudes radially outward or radially inward relative to an outer surface of the stem and has a distal surface configured for engaging one or more engagement pins of the piston during movement of the piston in a proximal direction.

15. The syringe assembly of claim 8, wherein the thickness of the concave end wall increases in a radially inward direction.

16. The syringe assembly of claim 8, wherein the cap has a nozzle in fluid communication with the interior volume of the rolling diaphragm syringe, wherein the nozzle has a connector for connecting to a fluid path set.

17. The syringe assembly of claim 16, wherein the connector is a luer connector.

18. A rolling diaphragm syringe for receiving a medical fluid therein, the rolling diaphragm syringe comprising:
   a proximal end comprising a concave end wall for engagement with a piston of a fluid injector, the proximal end comprising a radiused folding edge and wherein at least a portion of the concave end wall has non-uniform thickness;
   a distal end having an open-ended discharge neck;
   a sidewall extending between the proximal end and the distal end along a longitudinal axis, wherein the sidewall of the rolling diaphragm syringe defines an interior volume for receiving the medical fluid therein;
   a piston engagement portion protruding proximally from a central portion of the concave end wall and configured for engagement with the piston of the fluid injector, wherein the piston engagement portion has a stem with a first end attached to the concave end wall and a second end extending proximally from the first end; and
   a cap secured to the discharge neck of the rolling diaphragm syringe, wherein the cap has a nozzle in fluid communication with the interior volume of the rolling diaphragm syringe,
   wherein the sidewall is flexible and rolls upon itself when acted upon by the piston such that an outer surface of the sidewall is folded in a radially inward direction as the piston is advanced from the proximal end to the distal end and wherein the outer surface of the sidewall is unfolded in a radially outward direction as the piston is retracted from the distal end to the proximal end.

\* \* \* \* \*

UNITED STATES PATENT AND TRADEMARK OFFICE
CERTIFICATE OF CORRECTION

PATENT NO. : 10,933,190 B2
APPLICATION NO. : 15/568505
DATED : March 2, 2021
INVENTOR(S) : Berry et al.

It is certified that error appears in the above-identified patent and that said Letters Patent is hereby corrected as shown below:

In the Specification
In Column 8, Line 23, delete "180" and insert -- 180° --, therefor.
In Column 12, Line 17, delete "polyproplylene" and insert -- polypropylene --, therefor.
In Column 12, Line 18, delete "polyproplylene" and insert -- polypropylene --, therefor.
In Column 12, Line 18, delete "polyproplylene" and insert -- polypropylene --, therefor.
In Column 12, Line 40, delete "blow-mold-seal (BFS)" and insert -- Blow-Fill-Seal (BFS) --, therefor.
In Column 18, Lines 26-27, delete "syringe syringe" and insert -- syringe --, therefor.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*